US012690859B2

(12) United States Patent
    Osawa et al.

(10) Patent No.: US 12,690,859 B2
(45) Date of Patent: Jul. 28, 2026

(54) SUTURING DEVICE AND SUTURING METHOD

(71) Applicant: Brother Kogyo Kabushiki Kaisha, Nagoya (JP)

(72) Inventors: Naokatsu Osawa, Nagoya (JP); Ryuta Iijima, Nagoya (JP); Masashi Ichihashi, Mizuho (JP); Junji Yamano, Kariya (JP); Shigeki Yoshida, Toyoake (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 281 days.

(21) Appl. No.: 18/361,992

(22) Filed: Jul. 31, 2023

(65) Prior Publication Data

US 2023/0371943 A1 Nov. 23, 2023

Related U.S. Application Data

(63) Continuation of application No. PCT/JP2022/003752, filed on Feb. 1, 2022.

(30) Foreign Application Priority Data

Feb. 3, 2021 (JP) ................................. 2021-016121

(51) Int. Cl.
    *A61B 17/04* (2006.01)
    *A61B 17/06* (2006.01)
(52) U.S. Cl.
    CPC ...... *A61B 17/0469* (2013.01); *A61B 17/0482* (2013.01); *A61B 2017/0472* (2013.01); *A61B 2017/06042* (2013.01)
(58) Field of Classification Search
    CPC ............ A61B 17/0469; A61B 17/0482; A61B 17/0483; A61B 17/0491; A61B 17/06;
    (Continued)

(56) References Cited

U.S. PATENT DOCUMENTS 4,600,007 A 7/1986 Lahodny et al.
4,644,953 A 2/1987 Lahodny et al.
(Continued)

FOREIGN PATENT DOCUMENTS

CN 101646819 A 2/2010
CN 106659497 A 5/2017
(Continued)

OTHER PUBLICATIONS

Oct. 24, 2024—(EP) Extended EP Search Report—EP App. 22749691.6.

(Continued)

*Primary Examiner* — Dianne Dornbusch
(74) *Attorney, Agent, or Firm* — Banner & Witcoff, Ltd.

(57) ABSTRACT

A suturing device includes a plurality of suture needles, a first-thread holding mechanism, a needle moving mechanism, and a thread turning structure. The thread turning structure is configured to locally turn a portion of a first thread hooked on a distal end portion of each of a plurality of suture needles in the first thread stretched in a first direction around a needle axis thereof such that the portion of the first thread extends in a direction along a third direction intersecting the first direction and a second direction, in a state where the plurality of suture needles have been moved in the second direction. Each of the plurality of suture needles has a side surface formed with a threading recessed groove extending through the side surface in the first direction in a state where each of the plurality of suture needles has been moved in the second direction.

15 Claims, 23 Drawing Sheets

(58) Field of Classification Search
CPC ............ A61B 17/06004; A61B 17/062; A61B
2017/047; A61B 2017/0472; A61B
2017/0477; A61B 2017/06042; D05B
55/04
See application file for complete search history.

(56) References Cited

U.S. PATENT DOCUMENTS

| | | | | |
|---|---|---|---|---|
| 5,843,126 A * | 12/1998 | Jameel | ................... | A61B 17/06 606/220 |
| 8,313,509 B2 * | 11/2012 | Kostrzewski | .... | A61B 17/06066 606/232 |
| 2003/0065336 A1 * | 4/2003 | Xiao | ................. | A61B 17/0469 606/144 |
| 2010/0043686 A1 | 2/2010 | Suzuki | | |
| 2011/0178536 A1 | 7/2011 | Kostrzewski | | |
| 2011/0301620 A1 * | 12/2011 | Di Betta | .......... | A61B 17/06066 606/144 |
| 2017/0095249 A1 | 4/2017 | Ichikawa et al. | | |
| 2020/0038013 A1 * | 2/2020 | De Rezende Neto | ...................... | A61B 17/0482 |
| 2021/0045733 A1 * | 2/2021 | Osawa | ............... | A61B 17/0482 |

FOREIGN PATENT DOCUMENTS

| | | |
|---|---|---|
| JP | S60-085736 A | 5/1985 |
| JP | 2011-147770 A | 8/2011 |
| JP | 2019-193716 A | 11/2019 |

OTHER PUBLICATIONS

Apr. 12, 2022—International Search Report—Intl App PCT/JP2022/003752.

Jul. 9, 2024—(JP) Notice of Reasons for Refusal—JP App 2021-016121, Eng Tran.

Aug. 3, 2023—International Preliminary Reprot on Patentability and Written Opinion—Intl App PCT/JP2022/003752, Eng Tran.

* cited by examiner

SECOND DIRECTION

FOURTH DIRECTION

THIRD DIRECTION

SIXTH DIRECTION

FIRST DIRECTION

FIFTH DIRECTION

SECOND
DIRECTION

SIXTH
DIRECTION ↔ THIRD
DIRECTION

FIFTH
DIRECTION

FIG. 5

SIXTH DIRECTION

FIRST DIRECTION ←→ FOURTH DIRECTION

THIRD DIRECTION

FIFTH DIRECTION

FIRST DIRECTION ⟷ FOURTH DIRECTION

SECOND DIRECTION

FIFTH DIRECTION

FIRST DIRECTION ← → FOURTH DIRECTION

SECOND DIRECTION

FIG. 10

SECOND DIRECTION

FIRST DIRECTION ⟷ FOURTH DIRECTION

FIFTH DIRECTION

SECOND DIRECTION

FIRST DIRECTION ⟵⟶ FOURTH DIRECTION

FIFTH DIRECTION

THIRD DIRECTION

FIRST DIRECTION ⟵⟶ FOURTH DIRECTION

SIXTH DIRECTION

FIG. 15

SIXTH DIRECTION

FIRST DIRECTION ← → FOURTH DIRECTION

THIRD DIRECTION

SECOND DIRECTION

FIRST DIRECTION ←——→ FOURTH DIRECTION

FIFTH DIRECTION

SECOND DIRECTION

FOURTH DIRECTION

FIRST DIRECTION

FIFTH DIRECTION

SIXTH DIRECTION

FIRST DIRECTION ← → THIRD DIRECTION

FOURTH DIRECTION

SIXTH DIRECTION

FIRST DIRECTION ←→ FOURTH DIRECTION

THIRD DIRECTION

SIXTH DIRECTION

FIRST DIRECTION ⟷ FOURTH DIRECTION

THIRD DIRECTION

SIXTH DIRECTION

FIRST DIRECTION ← → FOURTH DIRECTION

THIRD DIRECTION

SIXTH DIRECTION

FIRST DIRECTION ← → FOURTH DIRECTION

THIRD DIRECTION

SIXTH DIRECTION

FIRST DIRECTION ⟷ FOURTH DIRECTION

THIRD DIRECTION

SUTURING DEVICE AND SUTURING METHOD

REFERENCE TO RELATED APPLICATIONS

This is a continuation application of International Application No. PCT/JP2022/003752 filed on Feb. 1, 2022, which claims priority from Japanese Patent Application No. 2021-016121 filed on Feb. 3, 2021. The entire contents of the aforementioned applications are incorporated herein by reference.

BACKGROUND ART

A known a suturing device is capable of suturing an entire suture portion of a suture target at a stroke using a suture without using metal staples in suturing the suture target in a field of, for example, living body surgery.

The known suturing device includes a first casing, a second casing, a plurality of needles, a needle moving mechanism, and a thread hook. The first casing and a second casing are disposed so as to be movable toward and away from each other in order to sandwich therebetween a suture target. The plurality of needles are arranged in a row in the first casing with their distal end portions directed toward the second casing, and are capable of holding a suture at the distal end portions thereof. The needle moving mechanism moves the plurality of needles toward the second casing. The thread hook is disposed at the second casing, and is movable along an arrangement direction of the plurality of needles to catch the suture that has reached the second casing through the suture target by movement of the plurality of needles by the needle moving mechanism.

According to this suturing device, in response to the plurality of needles arranged in the first casing and holding the suture at the distal end portions thereof being moved toward the second casing by the needle moving mechanism in a state where the suture target is sandwiched between the first casing and the second casing that has been moved toward each other, the distal end portions of the plurality of needles are caused to reach the second casing through the suture target. In response to the thread hook being moved along the arrangement direction of the plurality of needles in this state, the thread hook is caused to pass through thread loops formed by the suture that has reached the second casing via the suture target by the plurality of needles and the thread loops are caught by the suture threaded through a distal end portion of the thread hook. Thus, stitches are placed in the suture target readily and securely using the suture by a mechanical action achieved by a simple operation.

DESCRIPTION

However, in the known suturing device, prior to the suturing of the suture portion, an exacting setting operation may be required in which portions of the suture placed along the arrangement direction of the suture needles are hooked on the distal end portions of the suture needles such that the suture locally extends in a direction perpendicular to the arrangement direction of the suture needles. Therefore, this operation may interfere with shortening of the suturing time.

Accordingly, aspects of the disclosure provide a suturing device in which an operation of setting a suture to be performed prior to a suturing operation may be simple and a suturing operation time may be shortened.

In one or more aspects of the disclosure, a suturing device may include: a plurality of suture needles arranged in a row at certain intervals along a first direction, the plurality of suture needles each having a distal end portion formed with a thread hooking portion configured to allow a first thread to be hooked thereon; a first-thread holding mechanism to hold the first thread to be engaged with the plurality of suture needles; a needle moving mechanism to move the plurality of suture needles in a second direction intersecting the first direction, the second direction being a direction in which a distal end of each of the plurality of suture needles is directed; and a thread turning structure to locally turn a portion of the first thread hooked on the distal end portion of each of the plurality of suture needles in the first thread stretched in the first direction around a needle axis thereof such that the portion of the first thread extends in a direction along the third direction intersecting the first direction and the second direction, in a state where the plurality of suture needles have been moved in the second direction. Each of the plurality of suture needles may have a side surface formed with a threading recessed groove extending through the side surface in the first direction in a state where each of the plurality of suture needles has been moved in the second direction.

According to the suturing device of the one or more aspects of the disclosure, the suturing device may include the thread turning structure to locally turn the portion of the first thread hooked on the distal end portion of each of the plurality of suture needles in the first thread stretched in the first direction around the needle axis thereof such that the portion of the first thread extends in the direction along the third direction intersecting the first direction and the second direction, in a state where the plurality of suture needles have been moved in the second direction. Each of the plurality of suture needles may have the side surface formed with the threading recessed groove extending through the side surface in the first direction in a state where each of the plurality of suture needles has been moved in the second direction. Prior to the suturing operation, in response to each of the plurality of suture needles being moved in the second direction in a state where the first thread is linearly stretched and engaged with the thread hooking portion of each of the plurality of suture needles, in the first thread stretched in the first direction, a portion of the first thread hooked on the thread hooking portion of each of the suture needles may be locally turned around the axis of each of the suture needles to extend in the direction along the third direction intersecting the first direction and the second direction by the thread turning structure. In this state, a thread loop may be formed at the opening of each of the threading recessed grooves extending through the respective suture needles in the first direction. Thus, suturing may be performed at a stroke by pulling the first thread or the second thread to be threaded through the thread loops. Prior to such a suturing operation, the operation of setting the first thread on the plurality of suture needles may be completed by hooking of the first thread in the linearly stretched manner on the thread hooking portion of each of the plurality suture needles as described above. Thus, the operation of setting the suture performed prior to the suturing operation may be simplified.

In one or more aspects of the disclosure, a suturing method of suturing a suture target with a plurality of suture needles arranged in a row at certain intervals along a first direction, each of the plurality of suture needles formed with a threading recessed groove extending through each of the plurality of suture needles in the first direction, each of the plurality of suture needles configured to allow a first thread to be hooked at a distal end portion of each of the plurality of suture needles, the suturing method may include: linearly hooking the first thread on the distal end portion of each of the plurality of suture needles along the first direction prior to puncturing of the suture target with the plurality of suture needles; puncturing the suture target with the plurality of suture needles and locally turning a portion of the first thread hooked on each of the plurality of suture needles such that the portion of the first thread extends in a third direction, thereby positioning the first thread at an opening of the threading recessed groove, the third direction being orthogonal to the first direction; moving a thread hook through the threading recessed groove of each of the plurality of suture needles in a fourth direction in a state where the first thread is hooked on a distal end portion of the thread hook that has been moved in the first direction, thereby threading the first thread through thread loops formed by the first thread at the plurality of suture needles, respectively, the fourth direction being opposite to the first direction; and removing the plurality of suture needles from the suture target.

In one or more aspects of the disclosure, a suturing method of suturing a suture target with a plurality of suture needles arranged in a row at certain intervals along a first direction, each of the plurality of suture needles formed with a threading recessed groove extending through each of the plurality of suture needles in the first direction, each of the plurality of suture needles configured to allow a first thread to be hooked at a distal end portion of each of the plurality of suture needles, the suturing method may include: linearly hooking the first thread on the distal end portion of each of the plurality of suture needles along the first direction prior to puncturing of the suture target with the plurality of suture needles; puncturing the suture target with the plurality of suture needles and locally turning a portion of the first thread hooked on each of the plurality of suture needles such that the portion of the first thread extends in a third direction, thereby positioning the first thread at an opening of the threading recessed groove, the third direction being orthogonal to the first direction; moving a thread hook through the threading recessed groove of each of the plurality of suture needles in a fourth direction in a state where a second thread is hooked on a distal end portion of the thread hook that has been moved in the first direction, thereby threading the second thread through thread loops formed by the first thread at the plurality of suture needles, respectively, the fourth direction being opposite to the first direction; and removing the plurality of suture needles from the suture target.

According to the suturing methods of the one or more aspects of the disclosure, prior to the suturing operation, in response to each of the plurality of suture needles being moved in the second direction in a state where the first thread may be linearly stretched and engaged with the thread hooking portion of each of the plurality of suture needles, in the first thread stretched in the first direction, a portion of the lower thread hooked on the thread hooking portion of each of the suture needles may be locally turned around the axis of each of the suture needles to extend in the direction along the third direction intersecting the first direction and the second direction by the thread turning structure. In this state, thread loops may be formed at the openings of the threading recessed grooves extending through the suture needles in the first direction. Thus, suturing may be performed at a stroke by moving the thread hook through the threading recessed grooves to thread the first lower thread or the second thread into the thread loops. Prior to such a suturing operation, the operation of setting the first thread on the plurality of suture needles may be completed by hooking of the first thread in the linearly stretched manner on the thread hooking portion of each of the plurality suture needles as described above. Thus, the operation of setting the suture performed prior to the suturing operation may be simplified.

FIG. 5 is a plan view illustrating a plane of the suturing device of FIG. 3.

FIG. 10 is an enlarged view of the main body of the first casing constituting the suturing device of FIG. 1, and is a cross-sectional view taken along line X-X of FIG. 9.

FIG. 15 is a view for explaining an operation of the suturing device of FIG. 1, and is a view for explaining a suturing preliminary step for setting a lower thread.

Figure 1:
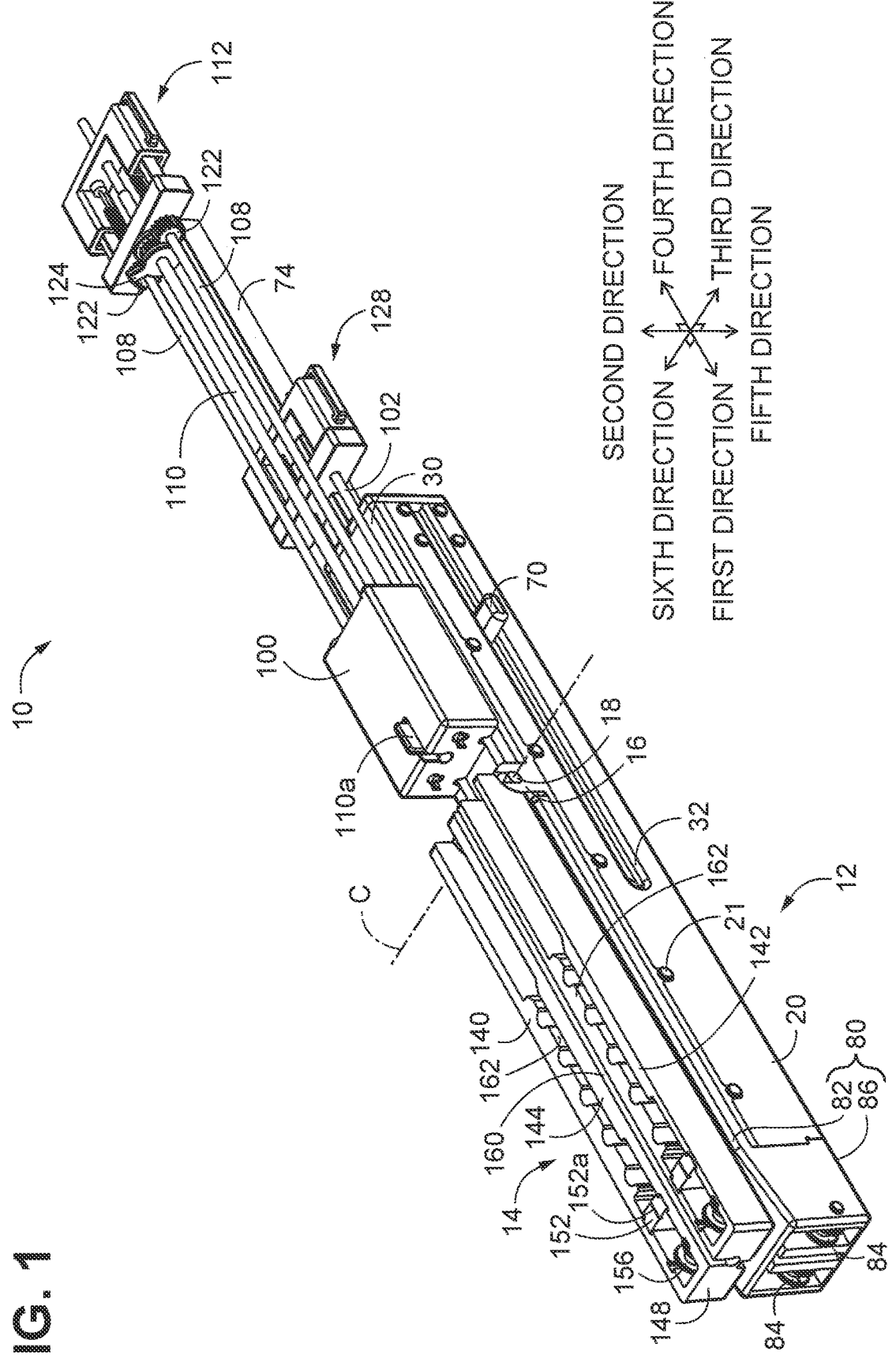
FIG. 1 is a general perspective view illustrating a suturing device.
Figure 22:
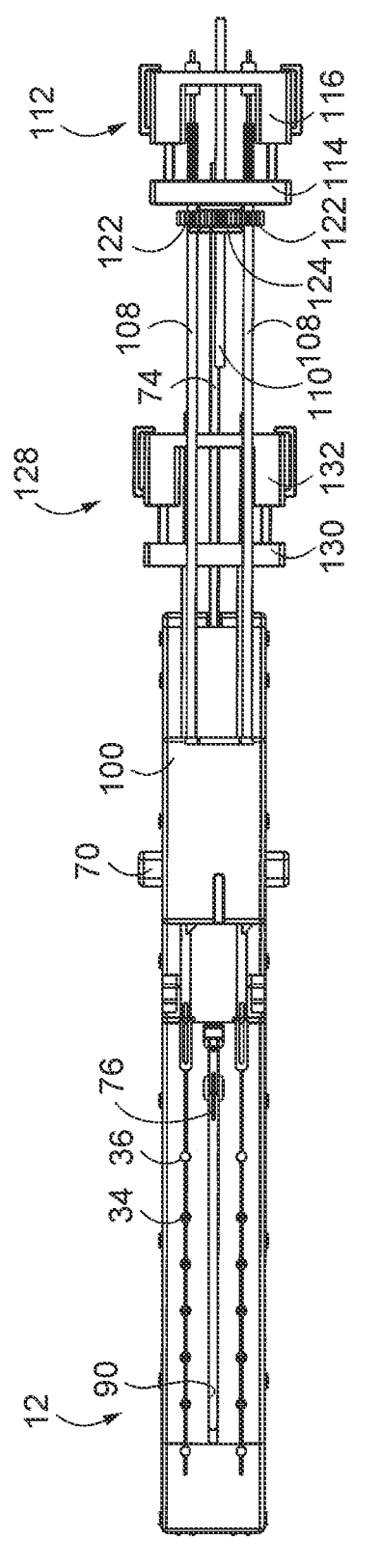

FIG. 22 is a view for explaining the operation of the suturing device of FIG. 1, wherein the upper-thread hooks are moved backward in a fourth direction toward their original positions by the backward movement operation of the upper-thread hook operating portion, a needle operating member is operated such that the suture needles are retracted into the first casing but the thread cutting needles are left standing in the first casing, and lower threads are tightened by a backward movement of lower-thread hooks while the lower-thread hooks hold the lower threads by a forward movement of a pipe connecting member of the lower-thread hook operating portion.

Figure 23:
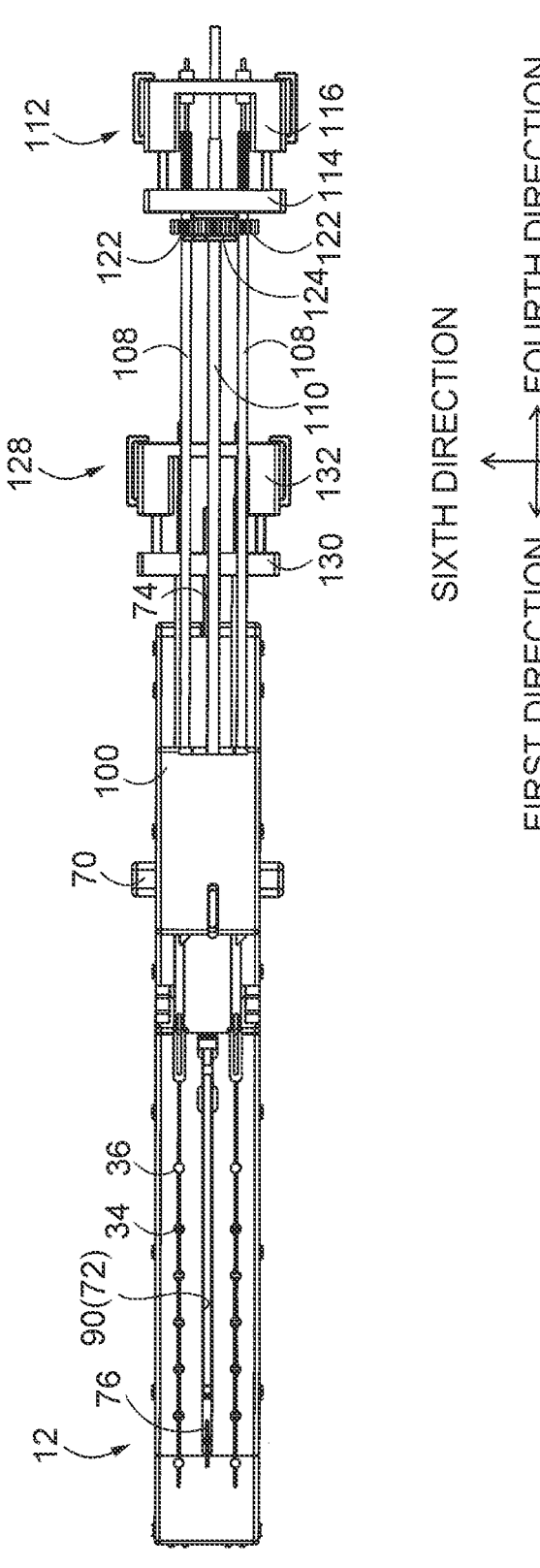

FIG. 23 is a view for explaining the operation of the suturing device of FIG. 1, wherein a cutter is moved to a forward end by a cutter pusher to cut a suture target.

Figure 24:
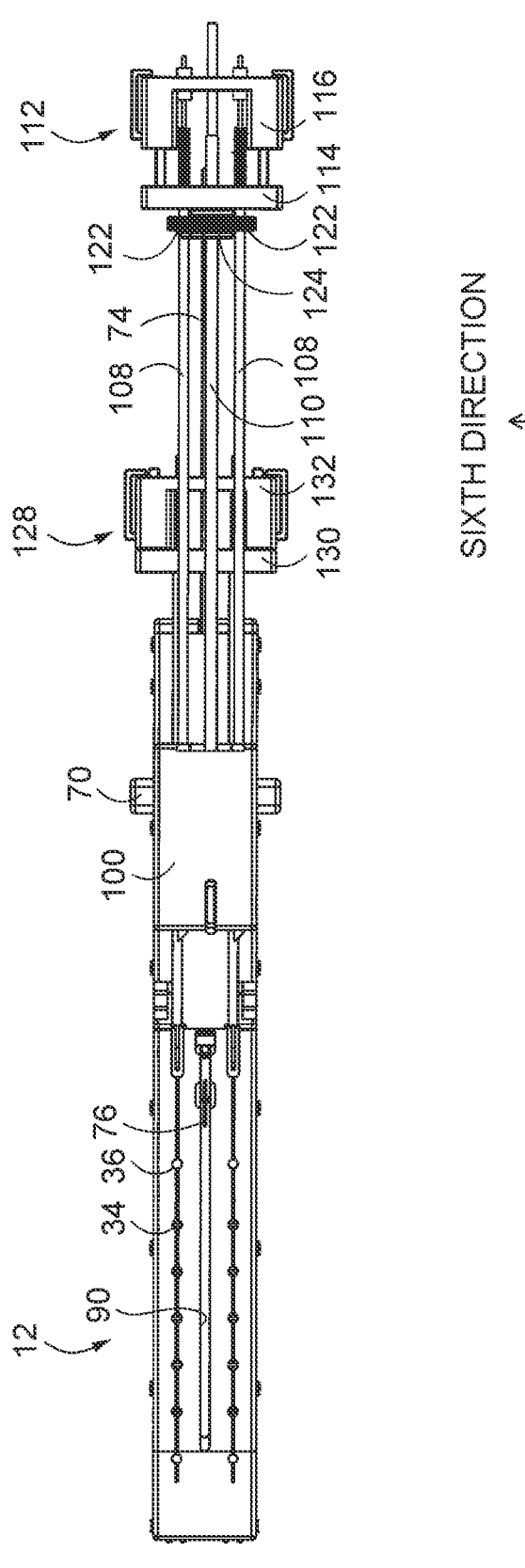

FIG. 24 is a view for explaining the operation of the suturing device of FIG. 1, wherein the needle operating member is further operated so as to move backward to retract the thread cutting needles into the first casing to cut the upper threads and the lower threads.

Figure 25:
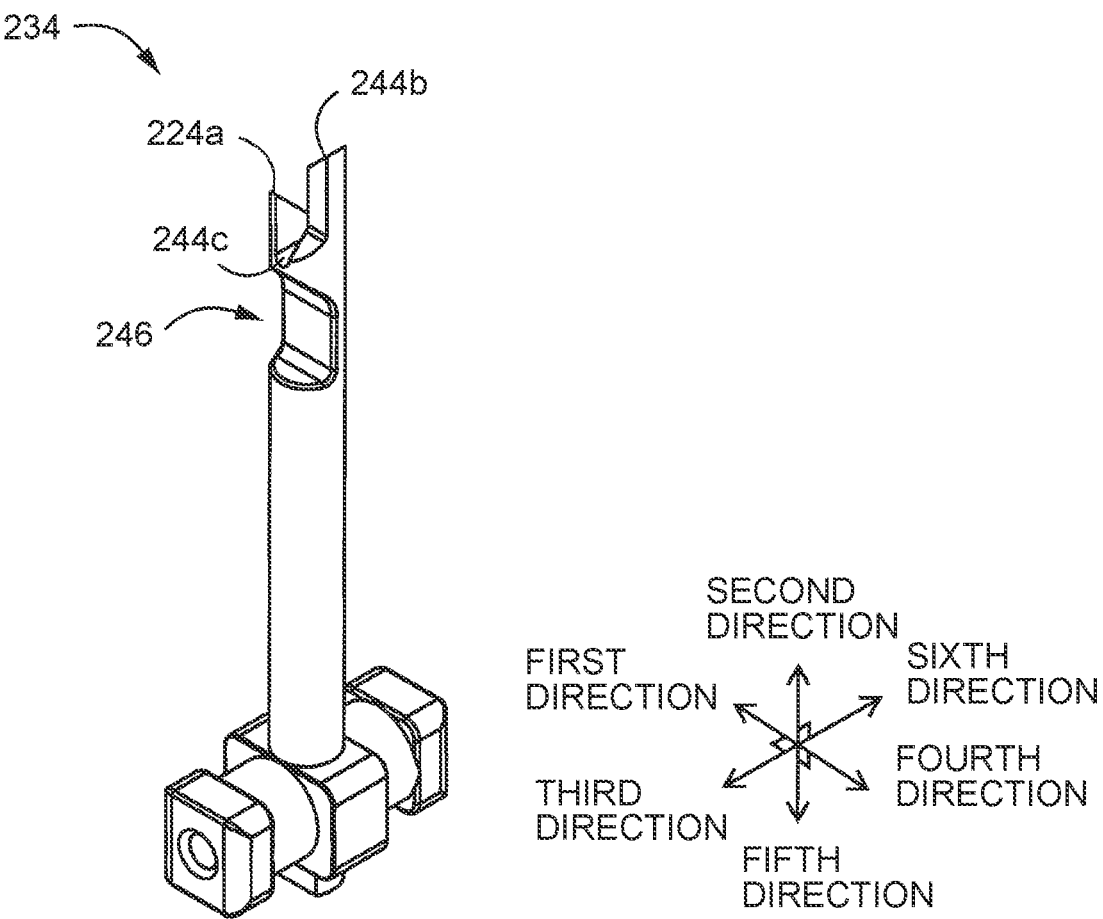

FIG. 25 is a perspective view illustrating another example of the suture needle used in the suturing device of FIG. 1.

Hereinafter, an illustrative embodiment of the disclosure will be described in detail with reference to the drawings. It should be noted that in the following illustrative embodiments, the drawings are for explaining essential parts relating to the disclosure, and dimensions, shapes, and the others are not always drawn accurately.

ILLUSTRATIVE EMBODIMENT 1

Figure 2:
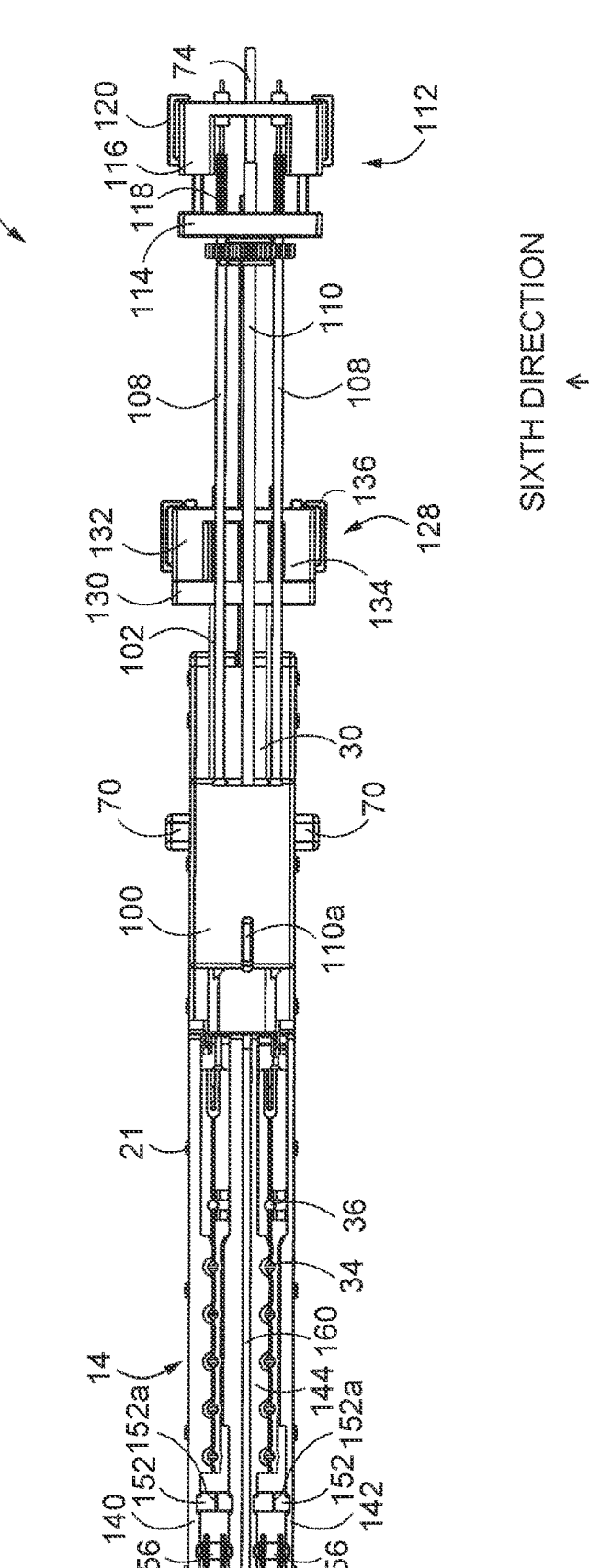
FIG. 2 is a plan view illustrating a plane of the suturing device of FIG. 1.
Figure 3:
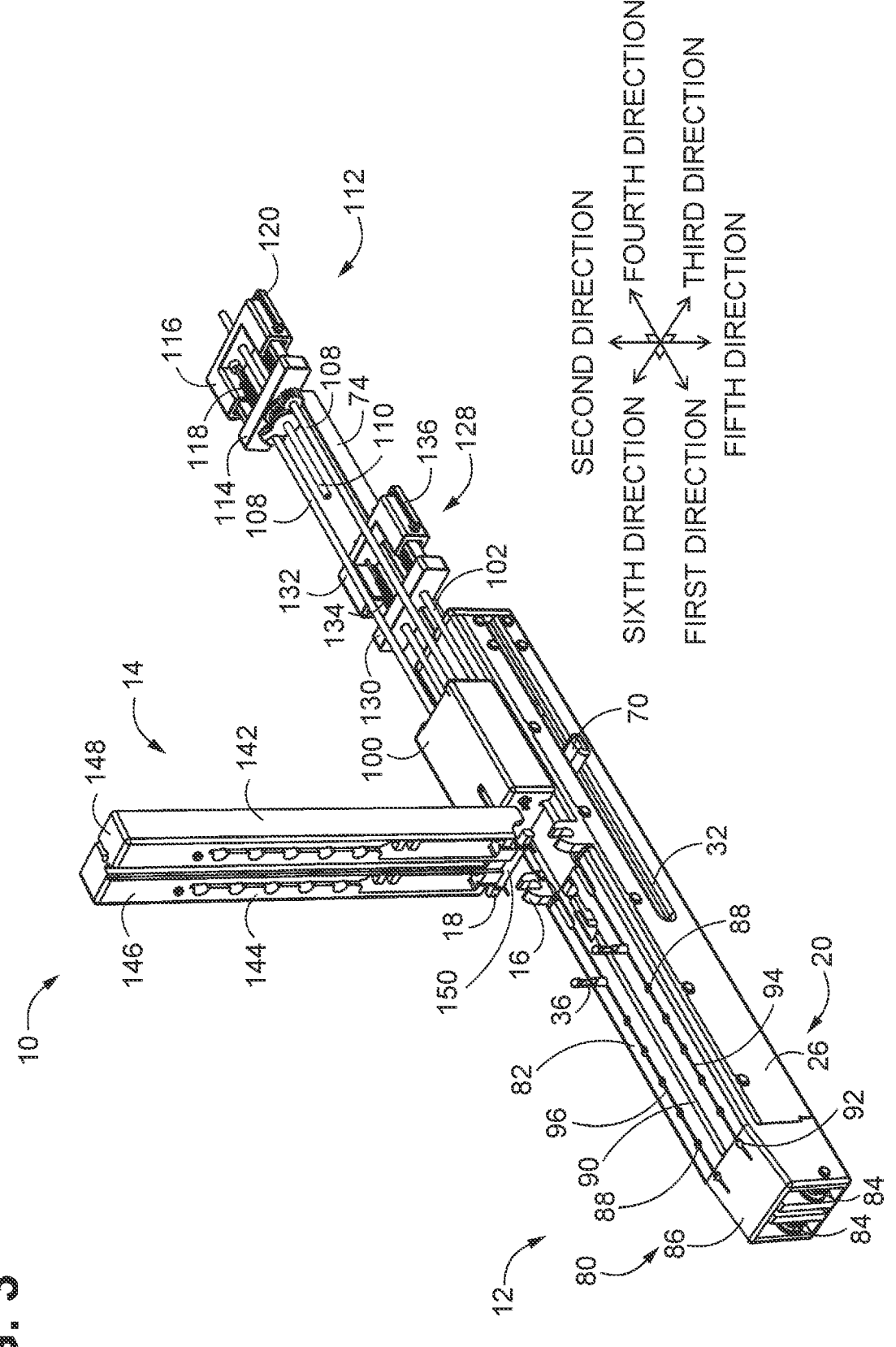
FIG. 3 is a perspective view illustrating the suturing device of FIGS. 1 and 2, wherein a second casing separated from a first casing is in a raised state with respect to the first casing.
Figure 4:
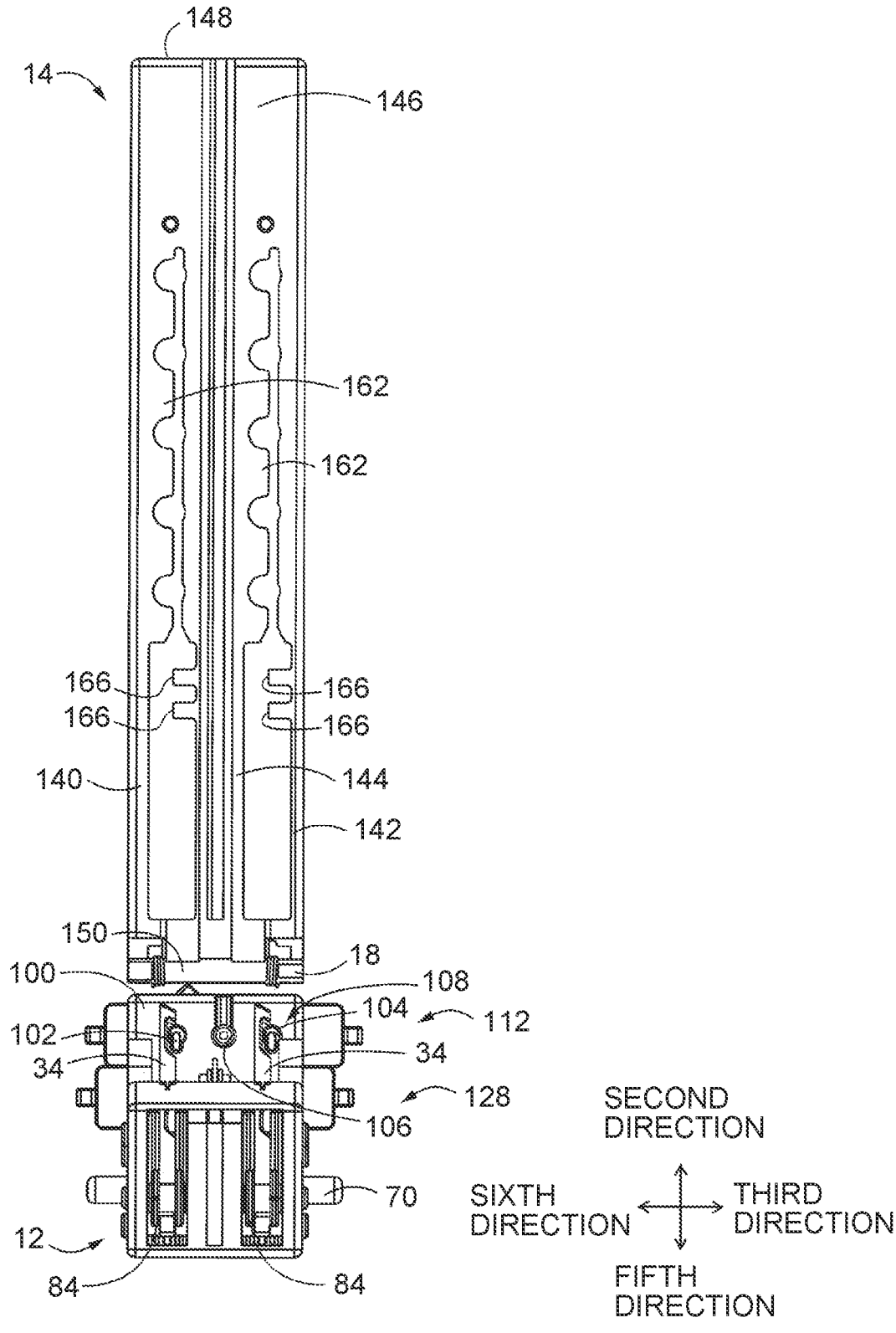
FIG. 4 illustrates the suturing device of FIG. 3 as viewed from a distal-end side of the first casing.
Figure 5:
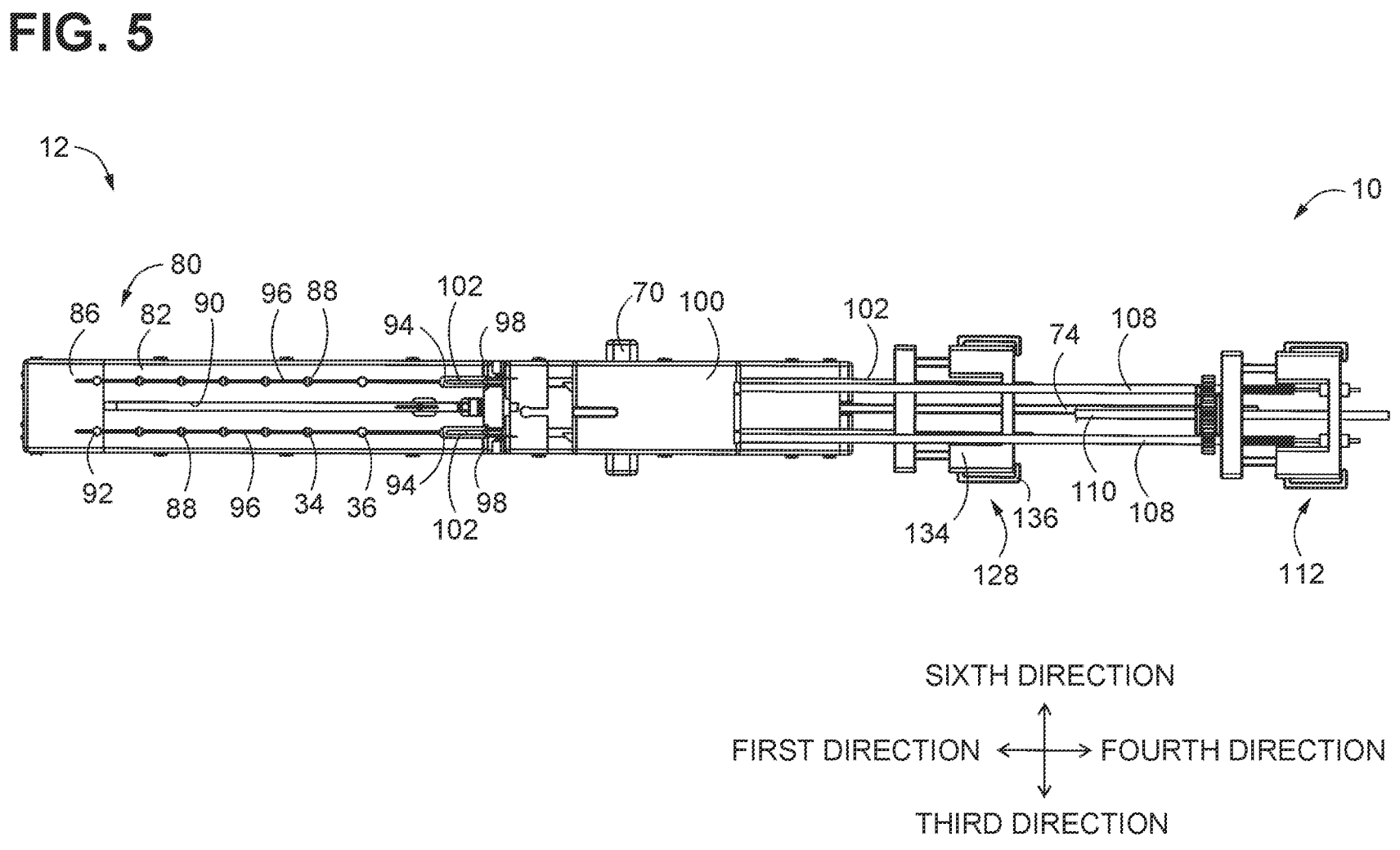
Figure 6:
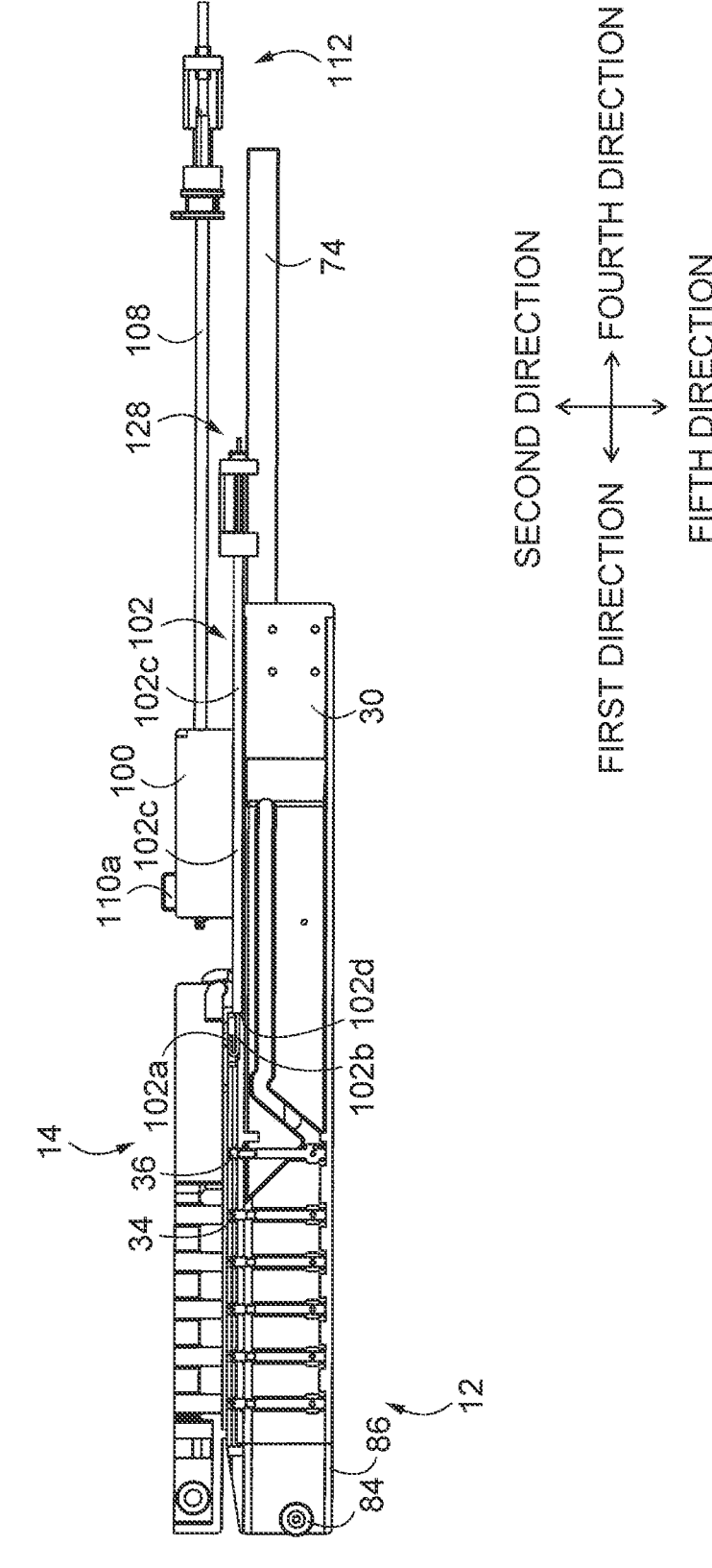
FIG. 6 is a cross-sectional view of the suturing device of FIG. 2, illustrating a cross-section through needle axes of suture needles.
Figure 7:
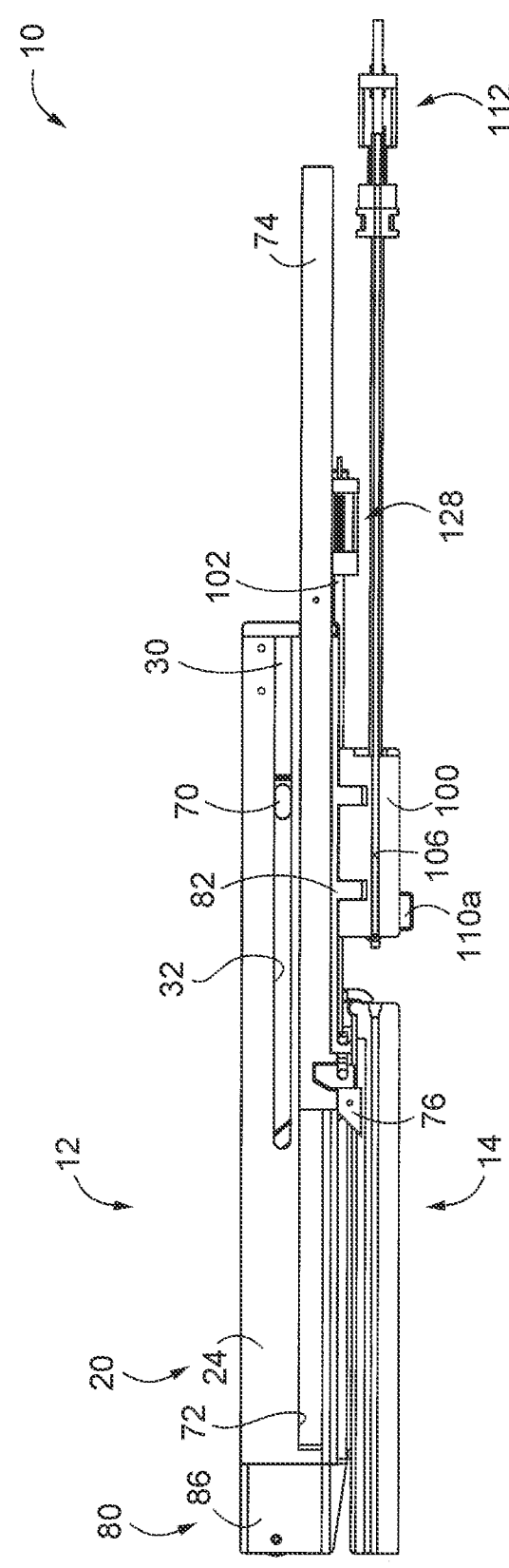
FIG. 7 is a cross-sectional view of the suturing device of FIG. 2, illustrating a cross-section through an axis of a cutter.
Figure 8:
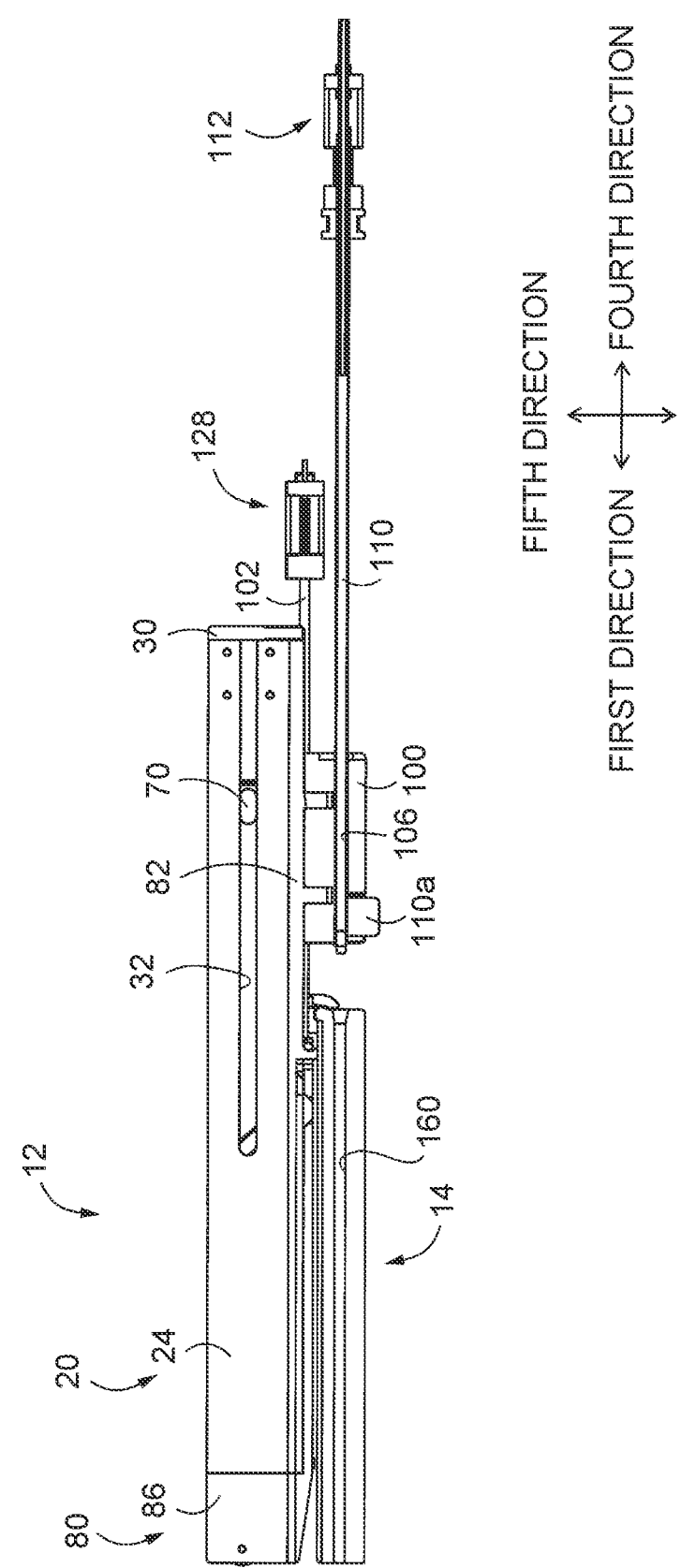
FIG. 8 is a cross-sectional view of the suturing device of FIG. 2, illustrating a cross-section through an axis of a locking pipe.

FIG. 1 is a perspective view illustrating essential parts of a suturing device 10 according to an illustrative embodiment of the disclosure. FIG. 2 is a plan view of the suturing device 10 as viewed from above in FIG. 1. FIG. 3 is a perspective view illustrating a state in which a second casing 14 is opened with respect to a first casing 12. FIG. 4 is a view illustrating a mating surface of the second casing 14 in a state where the second casing 14 is opened with respect to the first casing 12. FIG. 5 is a plan view illustrating the first casing 12 from which the second casing 14 is removed. FIG. 6 is a cross-sectional view of FIG. 2 through axes of suture needles 34. FIG. 7 is a cross-sectional view of FIG. 2 through a cutter 76. FIG. 8 is a cross-sectional view of FIG. 2 through a locking pipe 110.

As illustrated in FIGS. 1 to 8, the suturing device 10 includes the first casing 12 and the second casing 14 each having an elongated shape. The first casing 12 and the second casing 14 are connected to each other so as to be openable and closable, and each have a prismatic shape generally. The first casing 12 is integrally provided with bearings 16 having a C shape in a projecting manner at an intermediate portion of the first casing 12 in a longitudinal direction. The second casing 14 is integrally provided with pivot shafts 18 in a projecting manner at a proximal end of the second casing 14. The pivot shafts 18 are to be detachably received by the bearings 16. In a state where the pivot shafts 18 are supported by the bearings 16, the first casing 12 and the second casing 14 are coupled to each other so as to be relatively pivotable about their pivot axes C that are axes of the pivot shafts 18. The bearings 16 and the pivot shafts 18 function as an opening and closing mechanism for the first casing 12 and the second casing 14.

In the illustrative embodiment, as illustrated in FIG. 1, a direction toward a distal end of the suturing device 10 in the longitudinal direction of the suturing device 10 is referred to as a first direction. A direction toward a proximal end of the suturing device 10 and opposite to the first direction is referred to as a fourth direction. A direction from the first casing 12 toward the second casing 14 in a height direction of the suturing device 10, that is, an upward direction in FIG. 1, is referred to as a second direction. A direction from the second casing 14 toward the first casing 12 and opposite to the second direction is referred to as a fifth direction. A direction toward a near side in FIG. 1 in a width direction of the suturing device 10 and orthogonal to the first direction and the second direction is referred to as a third direction. A direction toward a far side in FIG. 1 and opposite to the third direction is referred to as a sixth direction. The pivot axes C of the pivot shafts 18 are parallel to the third direction or the sixth direction.

As illustrated in FIGS. 5 and 6, the first casing 12 includes a main body 20, a main body 20, a cover member 80, and an operating member support base 100. The main body 20 holds a plurality (e.g., five in the illustrative embodiment) of suture needles 34 and a single thread cutting needle 36. The cover member 80 is fixed to the main body 20 by bolts 21. The operating member support base 100 is fixed to the cover member 80. An interval between the centers of the plurality of suture needles 34 in their arrangement direction is constant. The thread cutting needle 36 is aligned with the plurality of suture needles 34 and disposed closer to the proximal-end side than the plurality of suture needles 34 while an interval between the center of the suture needle 34 and the center of the thread cutting needle 36 is greater than the interval between the centers of the plurality of suture needles 34.

Figure 9:
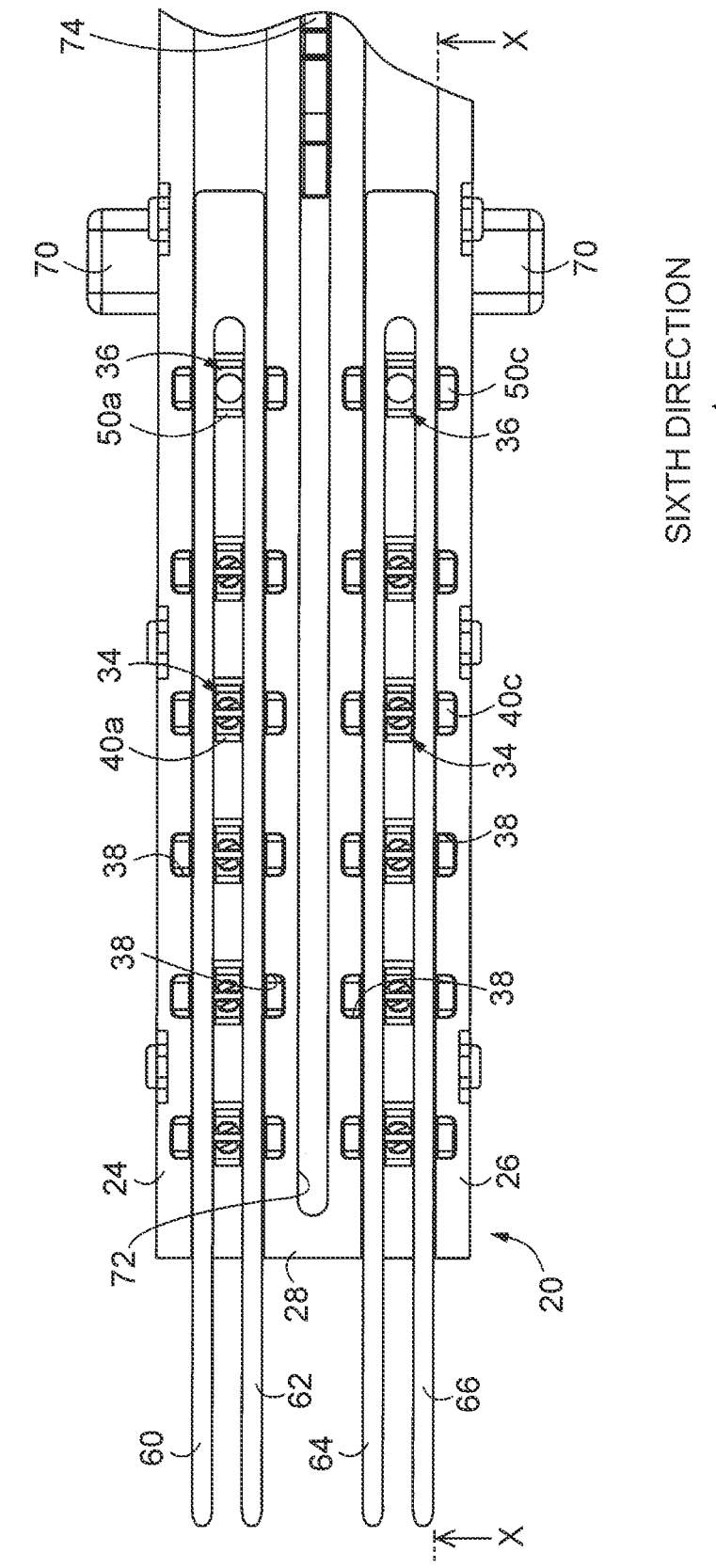
FIG. 9 is an enlarged plan view illustrating a main body of the first casing constituting the suturing device of FIG. 1.
Figure 10:
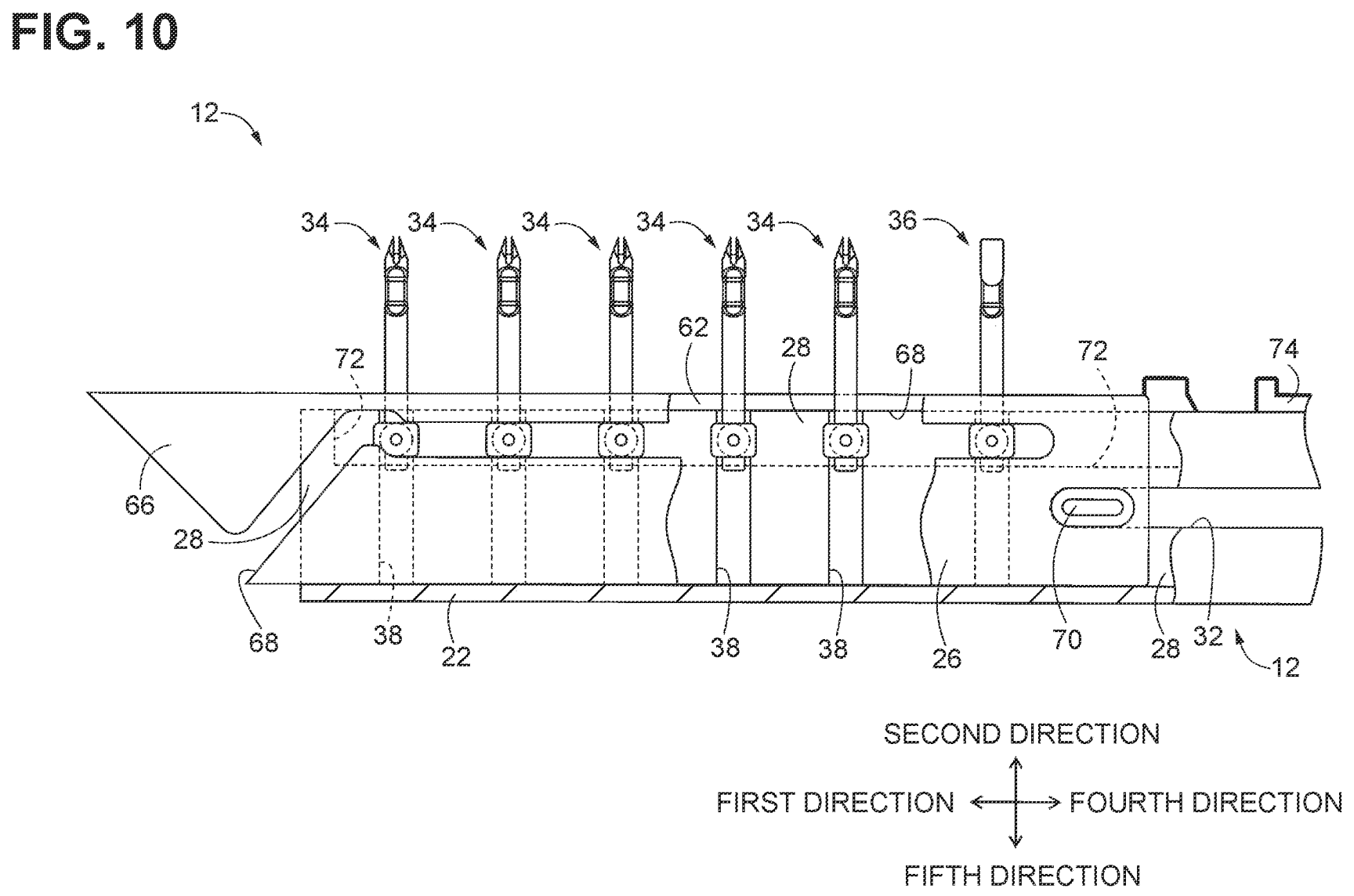

As illustrated in FIGS. 9 and 10, the main body 20 integrally includes an elongated bottom wall 22, a pair of elongated sidewalls 24 and 26, and an elongated central wall 28. The sidewalls 24 and 26 stand from respective ends of the bottom wall 22 in a width direction of the bottom wall 22. The central wall 28 stands from a middle of the bottom wall 22 in the width direction of the bottom wall 22 and extends in parallel with the sidewalls 24 and 26. Proximal end portions of the elongated sidewalls 24, 26 and the central wall 28 are fixed to each other with spacer members 30, illustrated in FIG. 1, being interposed between the sidewall 24 and the central wall 28 and between the sidewall 26 and the central wall 28, respectively. Further, each of the elongated sidewalls 24, 26 and the central wall 28 has an elongated hole 32 having a certain length in the first direction on the proximal-end side of the first casing 12 and extending therethrough in the width direction of the first casing 12.

Facing surfaces of the sidewall 24 and the central wall 28 and facing surfaces of the sidewall 26 and the central wall 28 each have a plurality of pairs of guide grooves 38 on a distal-end side of the first casing 12. The plurality of pairs of guide grooves 38 are for guiding, for example, the suture needles 34 illustrated in FIG. 11 and for example, the thread cutting needles 36 illustrated in FIG. 12. The plurality of pairs of guide grooves 38 are defined at certain intervals and are parallel to each other in the height direction of the suturing device 10.

Each suture needle 34 includes a proximal end portion 40, a distal end portion 44, and a threading recessed groove 46. The proximal end portion 40 supports the suture needle 34 such that the suture needle 34 is movable in the height direction of the suturing device 10 while its orientation in which the suture needle 34 is directed in the height direction of the suturing device 10 is maintained. The distal end portion 44 functions as a thread hooking portion for allowing a lower thread 42 corresponding to a first thread to be hooked thereon and also functions as a thread turning structure for locally turning the lower thread 42 caught by a distal end of the suture needle 34 around a needle axis CN of the suture needle 34 such that a direction in which the lower thread 42 extends is changed from the first direction to the third direction. Each suture needle 34 has a side surface between the proximal end portion 40 and the distal end portion 44. The threading recessed groove 46 extends through the side surface in the first direction.

The proximal end portion 40 of the suture needle 34 includes a rectangular parallelepiped needle stand 40a and a pair of protrusions 40b. The needle stand 40a is disposed at a proximal end of the suture needle 34. Each protrusion 40b protrudes from the needle stand 40a in the width direction of the first casing 12. The protrusion 40b is formed with a first engagement protrusion 40c and a second engagement protrusion 40d in this order from its distal end. The first engagement protrusion 40c has a rectangular cross section and is slidably engaged with a corresponding guide groove 38. The second engagement protrusion 40d has a circular cross section and is slidably engaged with a corresponding needle driving cam groove 68 illustrated in FIG. 10 and described later.

The distal end portion 44 of the suture needle 34 is formed with two apexes 44a and 44b, a third-direction guide groove 44c, and a pair of inclined guide surfaces 44d and 44e. The apexes 44a and 44b are spaced apart from each other by a distance less than a diameter of the suture needle 34 to allow the lower thread 42 extending in the first direction to pass therebetween. The third-direction guide groove 44c is in communication with a space between the two apexes 44a and 44b. The third-direction guide groove 44c extends in the third direction to guide a portion of the lower thread 42 that has passed between the two apexes 44a and 44b in the lower thread 42 extending in the first direction such that the portion of the lower thread 42 extends in the third direction. The inclined guide surfaces 44d, 44e obliquely extend from the apexes 44a and 44b, respectively, and along the third-direction guide groove 44c. The two apexes 44a and 44b are located on the respective sides of the third-direction guide groove 44c and are point symmetric with respect to the needle axis CN of the suture needle 34. The inclined guide surfaces 44d and 44e are located on the respective sides of the third-direction guide groove 44c and are point symmetric with respect to the needle axis CN of the suture needle 34. The apexes 44a and 44b and the third-direction guide groove 44c are connected by inclined surfaces. The third-direction guide groove 44c is formed in a convex shape at a position passing through the needle axis CN of the suture needle 34.

The threading recessed groove 46 has an inclined surface 46a, an inclined surface 46b, and a flat groove bottom 46c. The inclined surface 46a is disposed such that a groove bottom of the threading recessed groove 46 is shallower toward the distal end portion 44 of the suture needle 34. The inclined surface 46b is disposed such that the groove bottom of the threading recessed groove 46 is shallower toward the proximal end portion 40 of the suture needle 34. The groove bottom 46c is disposed between the inclined surface 46a and the inclined surface 46b and parallel to the needle axis CN.

Each thread cutting needle 36 includes a proximal end portion 50, a distal end portion 52, and a thread cutting recessed groove 54. The proximal end portion 50 has the same configuration as that of the proximal end portion 40 of each of the suture needles 34. The distal end portion 52 has a shape rounded into a hemispherical shape. Each thread cutting needle 36 has a side surface formed with the thread cutting recessed groove 54 extending through the side surface of the thread cutting needle 36 in the first direction. The proximal end portion 50 includes a rectangular parallelepiped needle stand 50a and a pair of protrusions 50b. The needle stand 50a disposed at a proximal end of the thread cutting needle 36. Each protrusion 50b protrudes from the needle stand 50a in the width direction of the first casing 12. The protrusion 50b is formed with a first engagement protrusion 50c and a second engagement protrusion 50d in this order from its distal end. The first engagement protrusion 50c has a rectangular cross section and is slidably engaged with a corresponding guide groove 38. The second engagement protrusion 50d has a circular cross section and slidably engaged with a corresponding needle driving cam groove 68 illustrated in FIG. 10.

In the thread cutting recessed groove 54, a distal-end-side sidewall 54a and a proximal-end-side sidewall 54b of the thread cutting needle 36 each have an inclined surface extending toward the distal end portion 52 of the thread cutting needle 36 as the inclined surface extends toward the groove bottom 54c. A peripheral edge of the distal-end-side sidewall 54a is formed with a cutting edge 56 obliquely extending such that the cutting edge 56 faces an opening of the thread cutting recessed groove 54 as the cutting edge 56 extends toward the proximal end portion 50 of the thread cutting needle 36.

As illustrated in detail in FIGS. 9 and 10, some of the plurality of suture needles 34 and one of the thread cutting needles 36 are arranged in a row at certain intervals along the first direction between the sidewall 24 and the central wall 28 and between the sidewall 26 and the central wall 28, respectively. A pair of needle driving plates 60, 62 is inserted between the sidewall 24 and the central wall 28 so as to be movable in the longitudinal direction of the suturing device 10 with the plurality of suture needles 34 and the single thread cutting needle 36 interposed therebetween. A pair of needle driving plates 64, 66 is inserted between the sidewall 26 and the central wall 28 so as to be movable in the longitudinal direction of the suturing device 10 with the plurality of suture needles 34 and the single thread cutting needle 36 interposed therebetween. Each of the needle driving plates 60, 62 and the needle driving plates 64, 66 is formed with a needle driving cam groove 68. In response to the second engagement protrusion 40d formed at the proximal end portion 40 of each of the suture needles 34 and the second engagement protrusion 50d formed at the proximal end portion 50 of the single thread cutting needle 36 being engaged with the needle driving cam grooves 68, the needle driving cam grooves 68 drive the suture needles 34 and the single thread cutting needle 36 in the height direction of the suturing device 10. The pair of needle driving plates 60, 62 and the pair of needle driving plates 64, 66 are connected to each other by a needle operating member 70 that partially protrude from side surfaces of the first casing 12 on the proximal-end side through the elongated holes 32.

Each of the needle driving cam grooves 68 of the needle driving plates 60, 62, 64, and 66 is formed such that a section corresponding to one arrangement pitch of the suture needles 34 obliquely extends toward the second direction and the other section extends linearly and flatly in the fourth direction as each of the needle driving cam grooves 68 extends from the distal-end side toward the proximal-end side. Thus, in response to the needle operating member 70 being operated in the first direction, the thread cutting needles 36 and the suture needles 34 are driven in the second direction in this order.

The needle driving plates 60, 62 and the needle driving plates 64, 66 operable in the longitudinal direction of the first casing 12 by the needle operating member 70, the second engagement protrusions 40d formed at the proximal end portions 40 of the suture needles 34 and are to be engaged with the needle driving cam grooves 68 formed in the needle driving plates 60, 62, 64 and 66, and the first engagement protrusions 40c formed at the proximal end portions 40 of the suture needles 34 and are in engagement with the guide grooves 38 formed in the facing surfaces of the sidewall 24 and the central wall 28 and the facing surfaces of the sidewall 26 and the central wall 28 function as a needle moving mechanism for moving the suture needles 34 in the height direction (e.g., the second direction) of the suturing device 10.

As illustrated in FIGS. 7 to 9, the central wall 28 has a cutter guide groove 72 in its second-direction-side surface, and a cutter 76 attached to a distal end of a cutter pusher 74 is configured to be moved along the cutter guide groove 72. The cutter pusher 74 is held by a lid plate portion 82 of the cover member 80 fixed to the main body 20 by the bolts 21 so as to be movable in the longitudinal direction. The cutter 76 is made of a thin steel plate, and is used, for example, for cutting between a pair of suture portions of a suture target T sandwiched between the first casing 12 and the second casing 14.

As illustrated in FIG. 1, the cover member 80 integrally includes the lid plate portion 82 and a box portion 86. The lid plate portion 82 covers the second-direction side of the first casing 12. The box portion 86 accommodates lower-thread bobbins 84 around each of which a lower thread 42 is wound, and covers the distal-end side of the main body 20 of the first casing 12. Each of the lower-thread bobbins 84 function as a thread holding mechanism that holds the lower thread 42 supplied for suturing.

Figure 15:
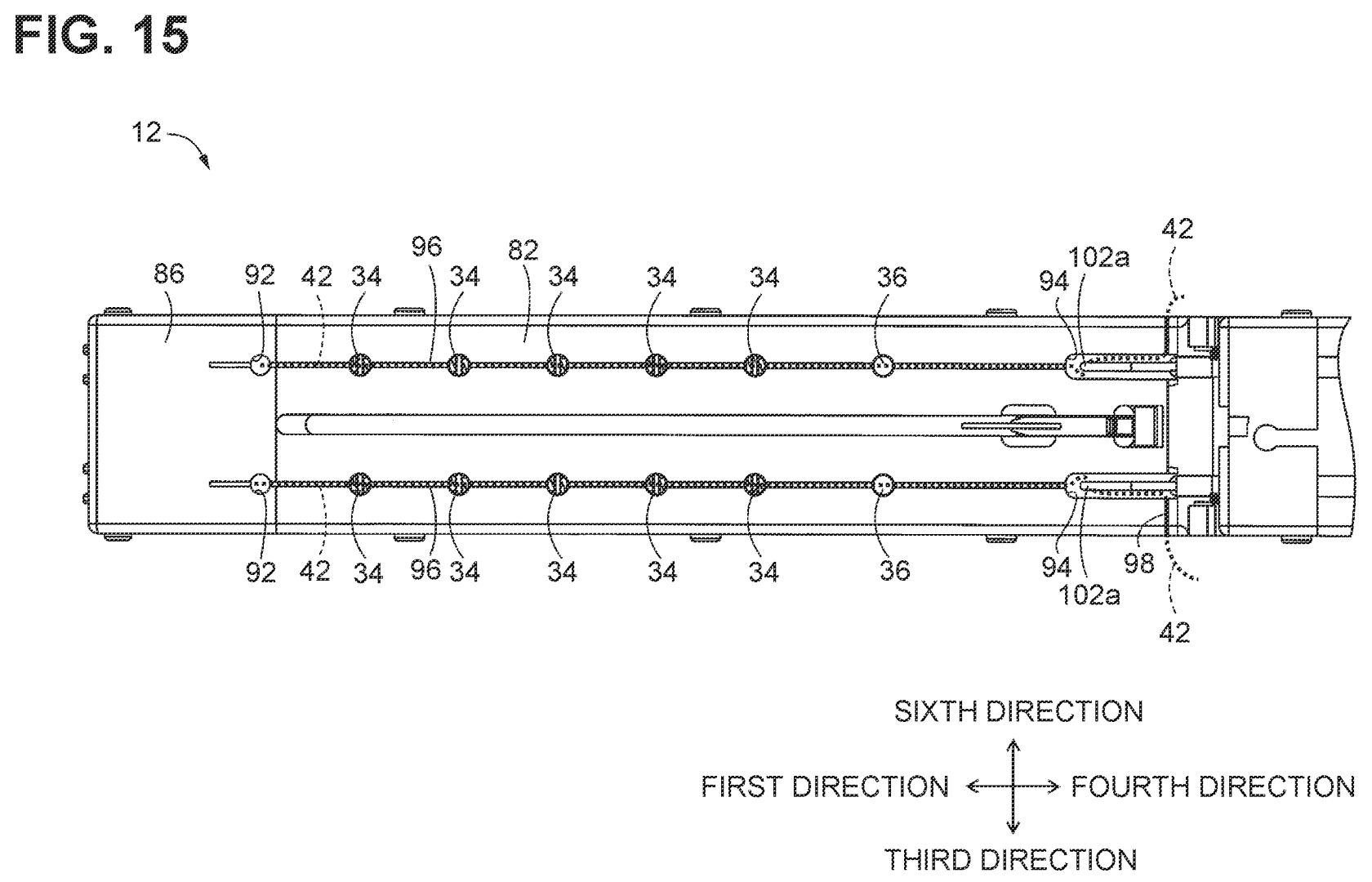
Figure 16:
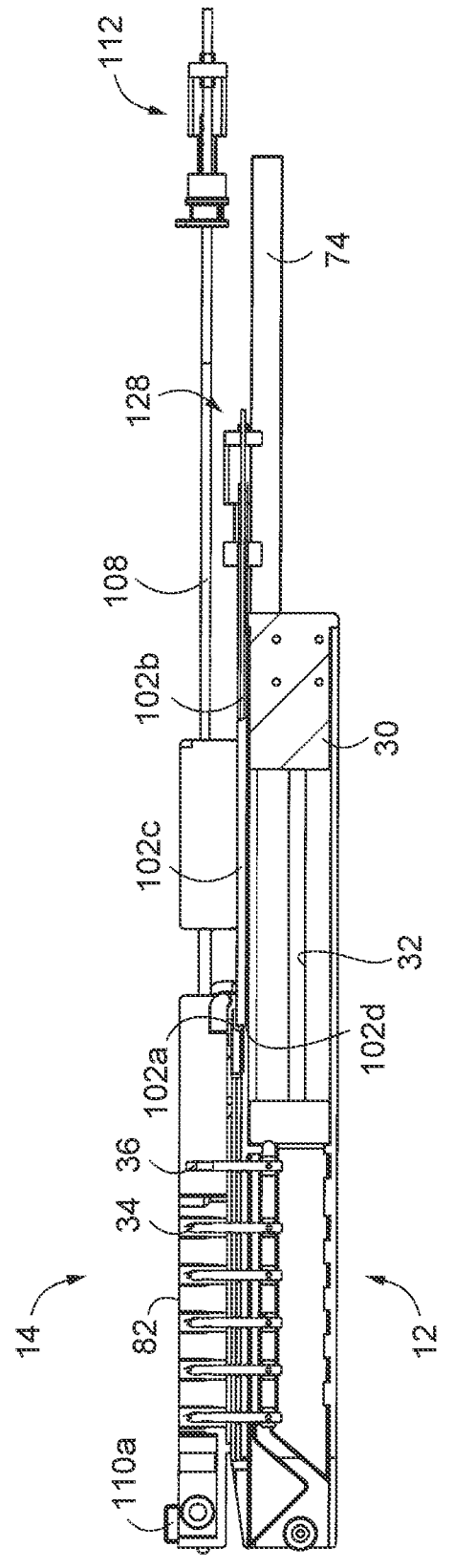
FIG. 16 is a view for explaining the operation of the suturing device of FIG. 1, and is a view for explaining a puncturing step or a lower-thread turning step.

As illustrated in FIGS. 3, 5, and other figures, the lid plate portion 82 is formed with a plurality of needle holes 88 that are arranged in two rows and allow the suture needles 34 and the thread cutting needles 36 to pass therethrough, and an elongated hole 90 that allows the cutter 76 to move therein. Among the plurality of needle holes 88, the needle holes 88 that allow the thread cutting needles 36 to pass therethrough function as cutting edges, each of which cuts the upper thread 138 and the lower thread 42 together with the cutting edge 56 formed at the thread cutting needle 36. As illustrated in FIGS. 1, 3 and 4, the box portion 86 accommodates the lower-thread bobbins 84, around each of which the lower thread 42 is wound, and has thread holes 92 through which the lower threads 42 drawn from the lower-thread bobbins 84, respectively, are taken out. Further, as illustrated in FIG. 5 and FIGS. 15 and 16 described later, the box portion 86 and the lid plate portion 82 have linear thread grooves 96. Each of the thread grooves 96 extends through the thread hole 92, the needle holes 88, and a cutout 94 accommodating a U-shaped hook portion 102a of a lower-thread hook 102. Each of the thread groove 96 is for allowing the lower thread 42 to be engaged therein to temporarily position the lower thread 42 in an initial setting operation. The lid plate portion 82 has thread retaining grooves 98 for temporarily retaining ends of the lower threads 42, respectively, in side edges thereof on the proximal-end side.

As illustrated in FIGS. 1 to 3 and 5 to 8, an operating member support base 100 having a thick plate-shape is fixed to the lid plate portion 82 of the cover member 80 at a position closer to the proximal-end portion side of the first casing 12 than an intermediate portion of the lid plate portion 82 in the longitudinal direction where the C-shaped bearings 16 protrude. The operating member support base 100 holds the pair of lower-thread hooks 102 such that the lower-thread hooks 102 are movable in the longitudinal direction between the operating member support base 100 and the lid plate portion 82 of the cover member 80 to which the operating member support base 100 is fixed. Further, as illustrated in FIG. 4, the operating member support base 100 is formed with a pair of upper-thread hook through holes 104 extending therethrough in the longitudinal direction of the first casing 12 and a locking pipe engagement hole 106 extending therethrough in the longitudinal direction of the first casing 12. The operating member support base 100 holds a pair of elongated upper-thread hooks 108 such that the upper-thread hooks 108 are slidable in the longitudinal direction in a state where the upper-thread hooks 108 extend through the upper-thread hook through holes 104, respectively. In addition, the operating member support base 100 holds a single elongated locking pipe 110 such that the locking pipe 110 is slidable in the longitudinal direction in a state where the locking pipe 110 extends through the locking pipe engagement hole 106. The locking pipe 110 includes a locking pipe operating portion 110a having a thickness less than a diameter of the locking pipe 110 at a distal end portion thereof.

As illustrated in FIG. 8, in response to the locking pipe 110 being inserted into a locking pipe guide groove 160 formed in the second casing 14, the locking pipe 110 restricts the first casing 12 and the second casing 14 from opening when the plurality of suture needles 34 penetrate the suture target T sandwiched between the first casing 12 and the second casing 14. The locking pipe 110 functions as a pivot prevention member. The locking pipe 110 and the locking pipe guide groove 160 function as a locking mechanism that prevents pivoting of the second casing 14 with respect to the first casing 12.

Figure 13:
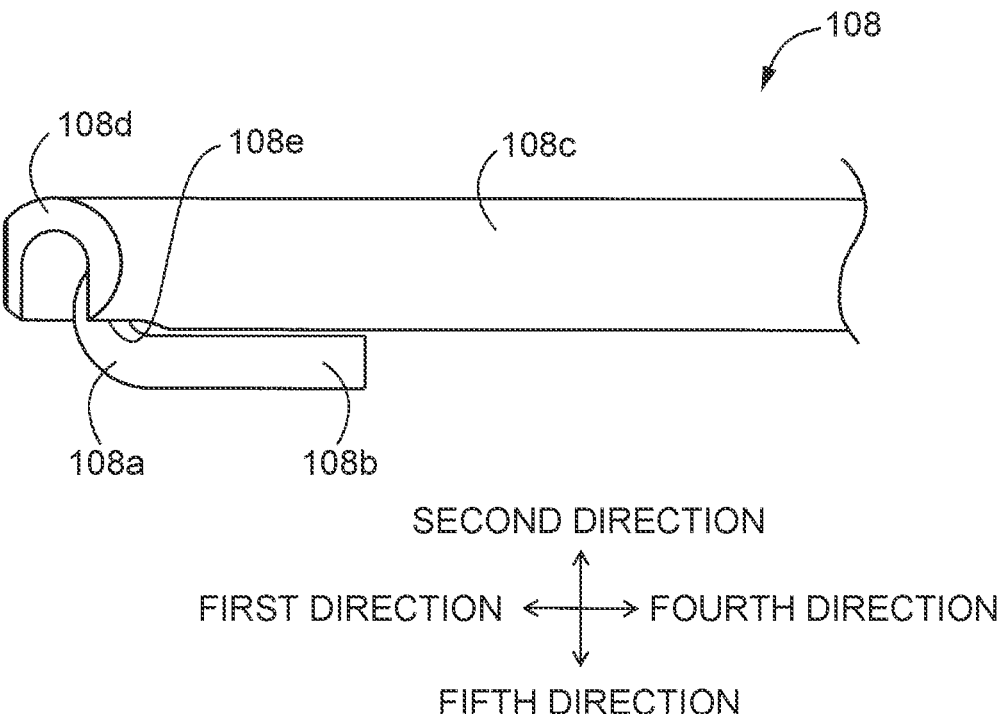
FIG. 13 is an enlarged front view illustrating a distal end portion of an upper-thread hook used in the suturing device of FIG. 1.
Figure 14:
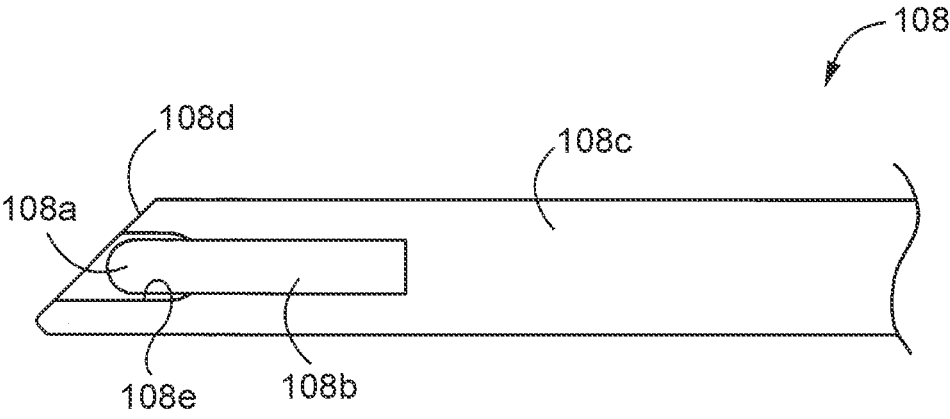
FIG. 14 is a bottom view illustrating the distal end portion of the upper-thread hook of FIG. 13.

As illustrated in detail in FIGS. 13 and 14, each of the upper-thread hooks 108 includes a hook wire 108b, a hook pipe 108c, and an upper-thread hook operating portion 112 illustrated in FIG. 1 and described later. The hook wire 108b is formed with a hook portion 108a that is a distal end thereof bent into a U-shape for catching the upper thread 138. The hook wire 108b is inserted in the hook pipe 108c.

The hook pipe 108c is a tubular member having an oblique end face 108d that is the distal end portion of the hook pipe 108c in the first direction cut obliquely in a plane including the first direction and the third direction such that a width of the hook pipe 108c in the third direction decreases toward the first direction. The oblique end face 108d opens in the first direction and the third direction. The end face 108d has a cutout 108e on the fifth direction side. The cutout 108e is to receive a portion to come into contact with the oblique end face 108d in the hook wire 108b constituting the hook portion 108a to cause the oblique end face 108d to be flat.

As illustrated in FIGS. 1 to 3, 5 to 8, and other figures, the upper-thread hook operating portion 112 includes a wire connecting member 114, a pipe connecting member 116, springs 118, a latching operation tool 120, a pair of gears 122, and an operation gear 124. The wire connecting member 114 connects proximal-end-side end portions of the pair of hook wires 108b such that the hook wires 108b are rotatable and are not movable in the longitudinal direction. The pipe connecting member 116 connects proximal-end-side end portions of the pair of hook pipes 108c such that the hook pipes 108c are rotatable and are not movable in the longitudinal direction. Each spring 118 is interposed between the wire connecting member 114 and the pipe connecting member 116 and urges the wire connecting member 114 and the pipe connecting member 116 in a direction in which the wire connecting member 114 and the pipe connecting member 116 are separated from each other, that is, in a direction in which the hook portions 108a of the hook wires 108b are pressed against the end faces 108d of the hook pipes 108c, respectively. The latching operation tool 120 latches the wire connecting member 114 and the pipe connecting member 116 to prevent the wire connecting member 114 and the pipe connecting member 116 from moving away from each other. The gears 122 are fixed to proximal end portions of the hook pipes 108c. The operation gear 124 is in mesh with the gears 122.

As illustrated in FIG. 6, each lower-thread hook 102 includes a hook wire 102b, a hook pipe 102c, and a lower-thread hook operating portion 128. The hook wire 102b is formed with a hook portion 102a that is a distal end portion thereof bent into a U-shape for catching the lower thread 42. The hook pipe 102c has an end face cut at a right angle. The hook wire 102b is inserted into the hook pipe 102c. The lower-thread hook operating portion 128 is illustrated in detail in FIGS. 1 to 5, and other drawings.

As illustrated in FIGS. 3 and 6, the lower-thread hook operating portion 128 includes a wire connecting member 130, a pipe connecting member 132, springs 134, and a latching operation tool 136. The wire connecting member 130 connects proximal-end-side end portions of the pair of hook wires 102b such that the hook wires 102b are rotatable and are not movable in the longitudinal direction. The pipe connecting member 132 connects proximal-end-side end portions of the pair of hook pipes 102c such that the hook pipes 102c are rotatable and are not movable in the longitudinal direction. Each spring 134 is interposed between the wire connecting member 130 and the pipe connecting member 132 and urges the wire connecting member 130 and the pipe connecting member 132 in a direction in which the wire connecting member 130 and the pipe connecting member 132 are separated from each other, that is, in a direction in which the hook portions 102a of the hook wires 102b are pressed against end faces 102d of the hook pipes 102c, respectively. The latching operation tool 136 latches the wire connecting member 130 and the pipe connecting member 132 to prevent the wire connecting member 130 and the pipe connecting member 132 from moving away from each other.

As illustrated in FIG. 4, the second casing 14 integrally includes a pair of sidewalls 140 and 142, a central wall 144, a bottom wall 146, a front wall 148, and a proximal-end-portion connecting member 150. The sidewalls 140 and 142 are parallel to each other and have an elongated shape. The central wall 144 is disposed between the sidewalls 140 and 142 and parallel to the sidewalls 140 and 142. The bottom wall 146 connects distal end portions of the sidewalls 140, 142 and the central wall 144. The front wall 148 connects distal end faces of the sidewalls 140, 142 and the central wall 144. The proximal-end-portion connecting member 150 is formed with the pair of pivot shafts 18 in the width direction of the second casing 14 and connects proximal-end-side bottom portions of the sidewalls 140, 142 and the central wall 144.

As illustrated in FIGS. 1 to 4, a pair of detachable partition walls 152 is disposed at the distal end portion of the second casing 14. The partition walls 152 are disposed between the sidewall 140 and the central wall 144 and between the sidewall 142 and the central wall 144, respectively. The sidewall 140 or the sidewall 142, and the central wall 144, the bottom wall 146, the front wall 148, and one of the partition walls 152 form a pair of boxes that respectively accommodate a corresponding one of the pair of upper-thread bobbins 156, around each of which the upper thread 138 is wound. The pair of partition walls 152 each have an upper thread guide groove 152a in which the upper thread 138 drawn from the upper-thread bobbin 156 is to be positioned in advance at a position where the hook portion 108a of the upper-thread hook 108 that have been operated to move forward may catch the upper thread 138.

As illustrated in FIG. 1, the central wall 144 has a locking pipe guide groove 160 that allows the locking pipe 110 and the locking pipe operating portion 110a fixed to the distal end portion thereof to pass therethrough. The locking pipe guide groove 160 has a cross-sectional shape in which a circular cross-section slightly greater than the locking pipe 110 and a rectangular cross-section slightly thicker than the locking pipe operating portion 110a are connected.

As illustrated in FIG. 4, an inner wall surface of the sidewall 140 of the second casing 14 and a wall surface of the central wall 144 on the sidewall 140 side are provided with a plurality of upper-thread hook support portions 162 protruding therefrom for supporting the upper-thread hooks 108 from the third direction in order to stably move the upper-thread hooks 108 between the suture needles 34. A wall surface of the central wall 144 on the sidewall 140 side and an inner wall surface of the sidewall 142 are provided with pairs of thread pushing protrusions 166, respectively. In each pair, the thread pushing protrusions 166 protrude to both sides of the thread cutting needle 36 in the longitudinal direction of the second casing 14 and have inclined surfaces for moving the upper thread 138 pulled by the upper-thread hook 108 toward the thread cutting needle 36. The inclined surfaces of the pairs of thread pushing projections 166 are inclined toward the fifth direction as the inclined surfaces extend toward the fourth direction (e.g., a protruding direction). The upper threads 138 are reliably inserted into the thread cutting recessed grooves 54 of the thread cutting needles 36, respectively, in the process in which the thread cutting needles 36 are lowered in the fifth direction.

Next, referring to FIGS. 15 to 24, a description will be provided on an operation of suturing a suture target T with sutures L using the suturing device 10 configured as described above. The state in which the second casing 14 is opened from the first casing 12 illustrated in FIGS. 3, 4, and 5 illustrates an initial state of the suturing device 10 in which the pivot shafts 18 of the second casing 14 are slightly spaced from the bearings 16 of the first casing 12. Note that FIGS. 17 to 24 illustrate the first casing 12 from which the second casing 14 is removed.

Figure 11:
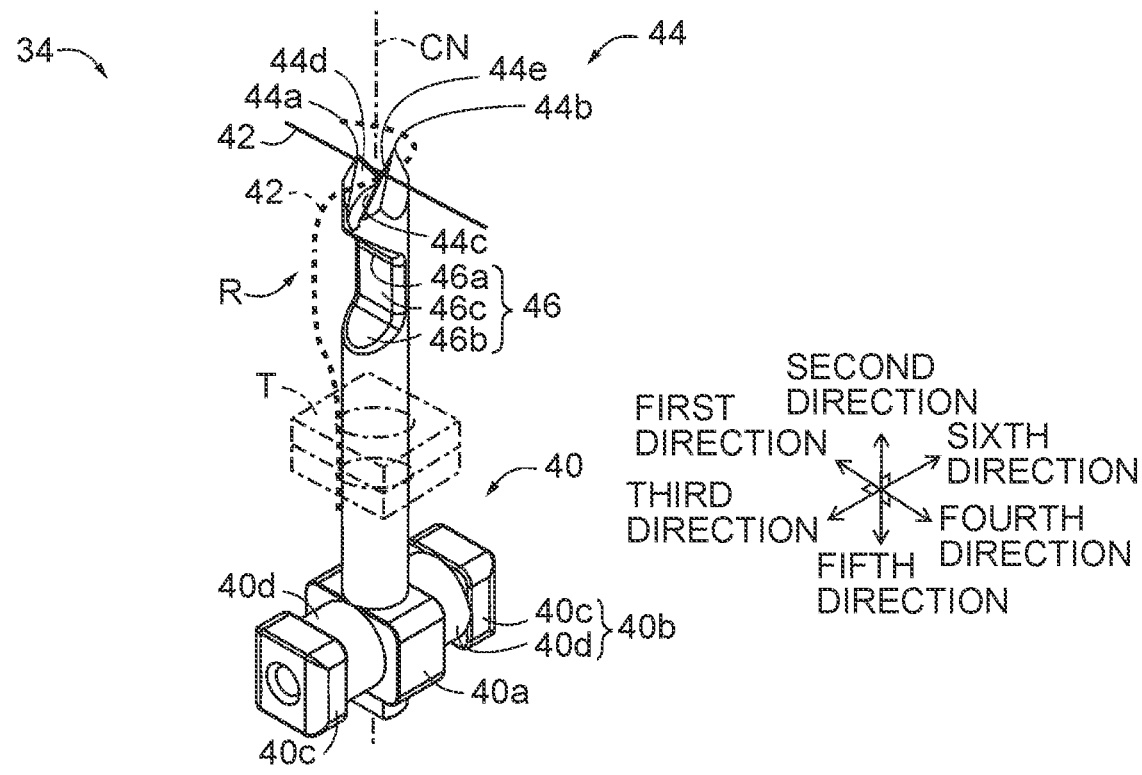
FIG. 11 is a perspective view illustrating a configuration of a suture needle used in the suturing device of FIG. 1.
Figure 12:
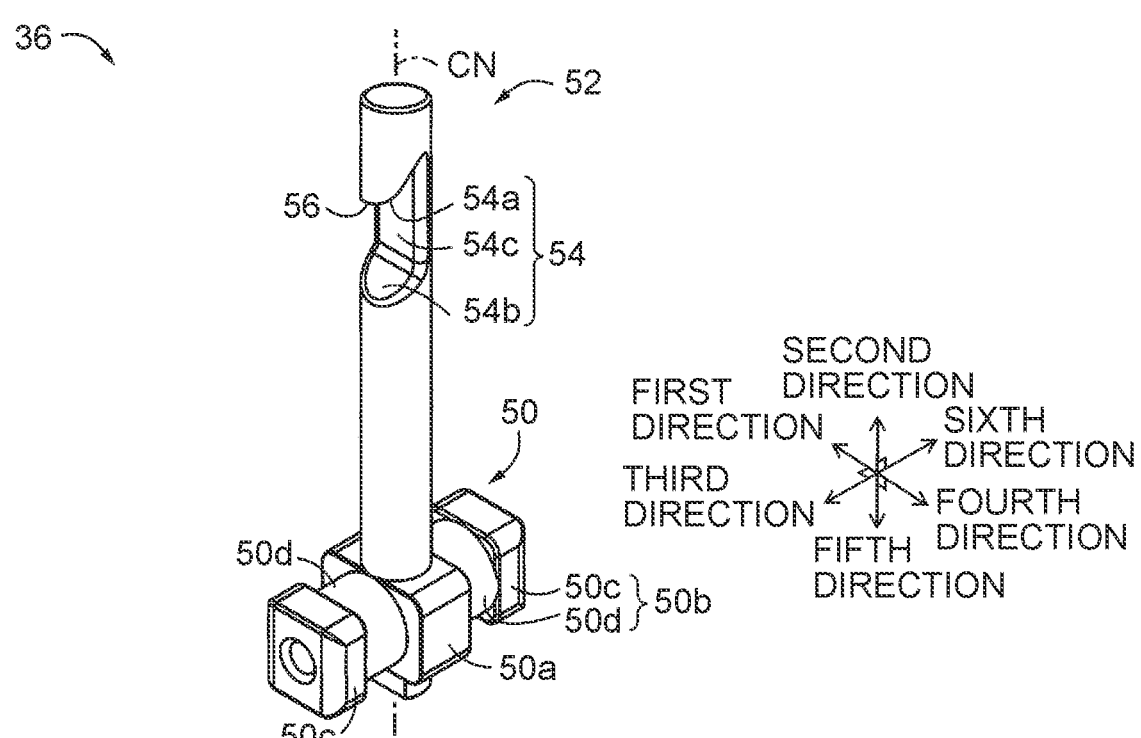
FIG. 12 is a perspective view illustrating a configuration of a thread cutting needle used in the suturing device of FIG. 1.

In this initial state, as illustrated in FIG. 15, the lower threads 42 are set in the first casing 12. The lower threads 42 wound around the lower-thread bobbins 84, respectively, in the box portion 86 are linearly drawn out from the respective thread holes 92, and are caught by the hook portions 102a of the lower-thread hooks 102, respectively. Thereafter, the lower threads 42 are pressed into and retained by the respective thread retaining grooves 98 formed in the side edges of the lid plate portion 82 on the proximal-end side. By such a simple operation of positioning the lower threads 42, the lower threads 42 extending in the first direction are hooked between the pair of apexes 44a and 44b of each suture needle 34 as illustrated in FIG. 11. FIG. 15 illustrates a first-thread hooking and setting step that is a suturing preparatory step.

Next, after the suture target T is inserted between the first casing 12 and the second casing 14 in this state, the first casing 12 and the second casing 14 are closed. Next, in response to the locking pipe operating portion 110*a* illustrated in FIG. 8 being operated in the first direction, the locking pipe 110 is inserted into the locking pipe guide groove 160 of the second casing 14, thereby locking the rotation of the second casing 14. Then, in response to the needle operating member 70 illustrated in FIG. 1 being operated in the first direction, the plurality of suture needles 34 and the thread cutting needles 36 are moved in the second direction to protrude from the lid plate portion 82 of the first casing 12. FIG. 16 illustrates this state with the suture target T being omitted.

In the state of FIG. 16, as illustrated in FIG. 11, in response to the lower thread 42 is pressed toward the proximal end portion 50 of each of the suture needles 34, the lower thread 42 extending in the first direction hooked between each pair of apexes 44*a* and 44*b* is turned by 90° around the needle axis CN of each of the suture needles 34 to locally extend in the width direction of the first casing 12, that is, in the third direction, thereby forming a thread loop R extending across the threading recessed groove 46 in the second direction. FIG. 16 corresponds to a puncturing step in which a portion hooked on the distal end portion 44 of each suture needle 34 in the lower thread 42 extending in the first direction is locally turned to extend in the third direction, or a lower-thread turning step.

Figure 17:
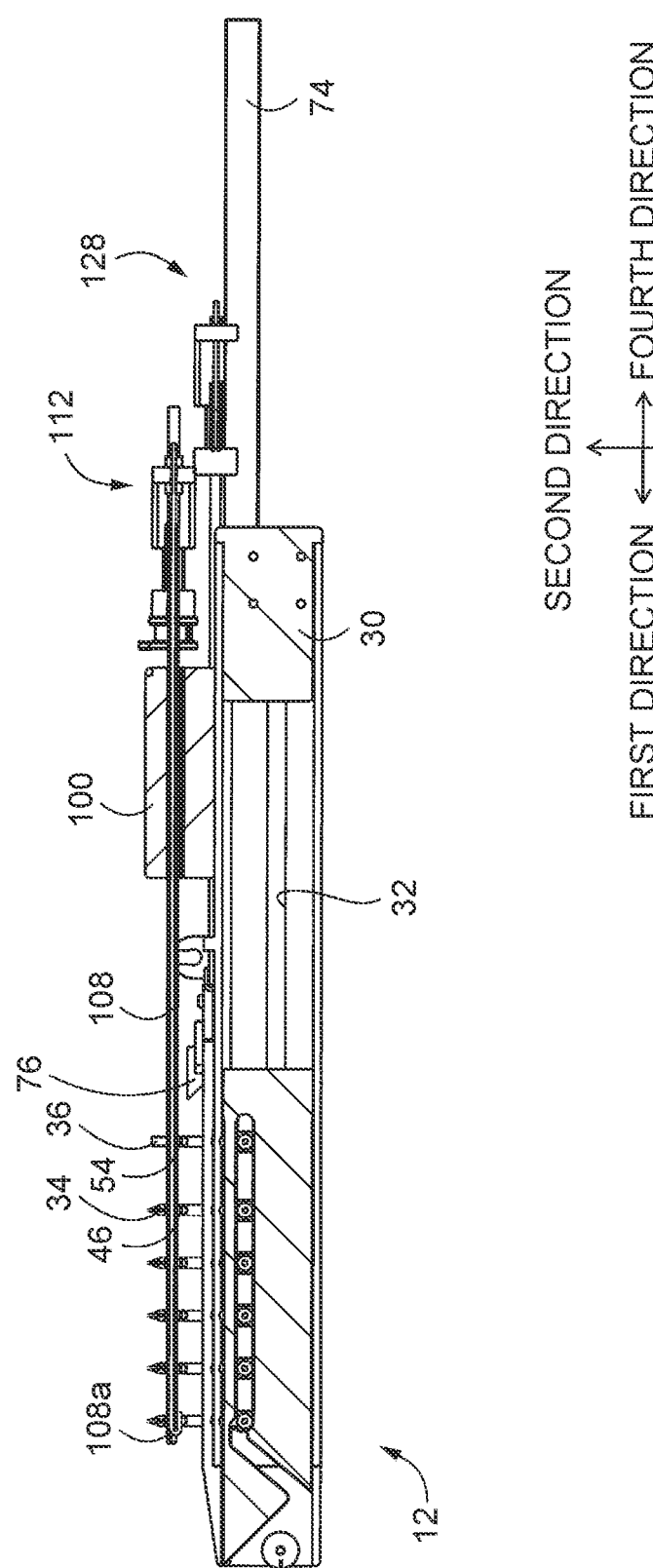
FIG. 17 is a view for explaining the operation of the suturing device of FIG. 1, wherein a pair of the upper-thread hooks are moved forward.

Next, an upper thread holding step is performed in which the upper-thread hooks 108 hold the upper threads 138, respectively, that have been drawn out in advance from the upper-thread bobbins 156 illustrated in FIG. 1 and positioned in advance by the upper-thread guide grooves 152*a* formed in the partition walls 152. First, as illustrated in FIG. 17, in response to the upper-thread hook operating portion 112 being operated in the first direction, the pair of upper-thread hooks 108 are moved forward. In this state, the distal end portion of each of the upper-thread hooks 108 passes through the thread cutting recessed groove 54 formed in the thread cutting needle 36 and the threading recessed grooves 46 formed in the suture needles 34. In each of the suture needles 34, the thread loop R extending across the threading recessed groove 46 in the second direction is formed, and thus the distal end portion of each of the upper-thread hooks 108 also passes through the thread loops R.

Figure 18:
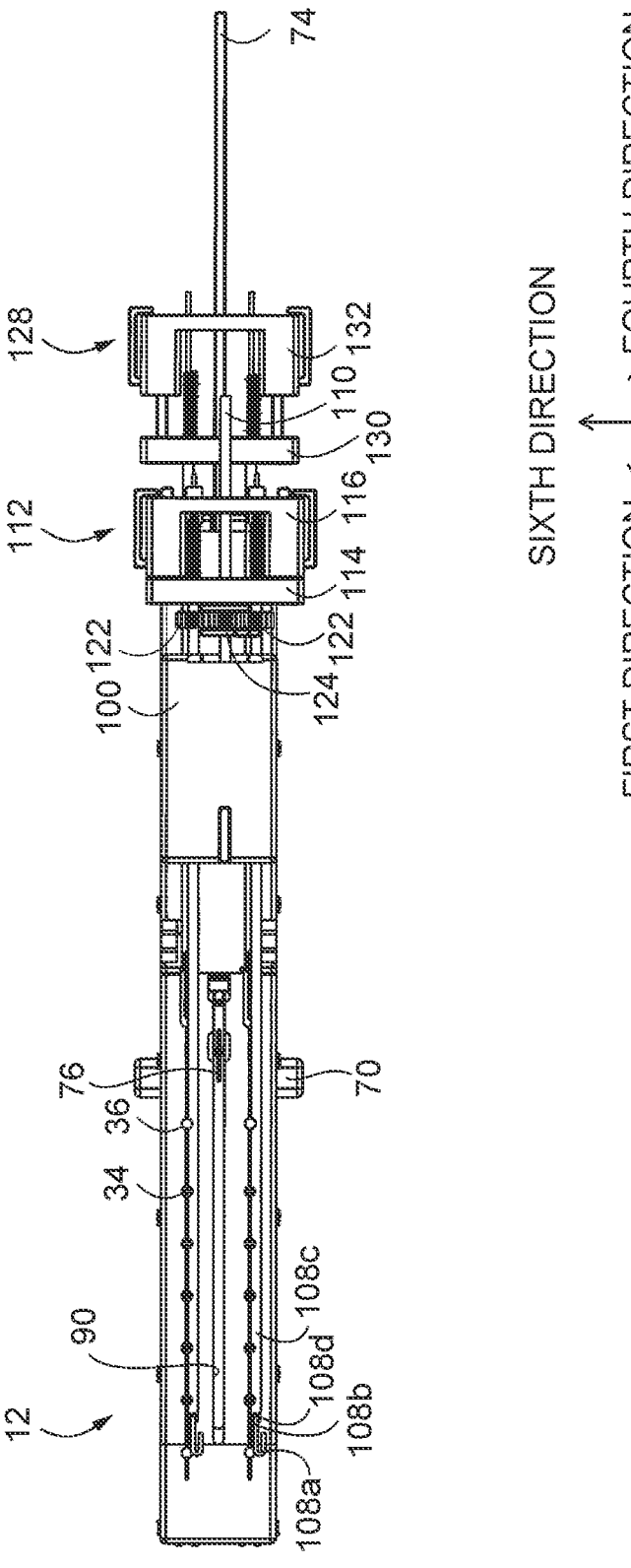
FIG. 18 is a view for explaining the operation of the suturing device of FIG. 1, wherein hook portions of hook wires protrude beyond oblique inclined faces of hook pipes after the upper-thread hooks moved forward are rotated to cause the hook portions of hook wires to be in a parallel horizontal orientation.
Figure 19:
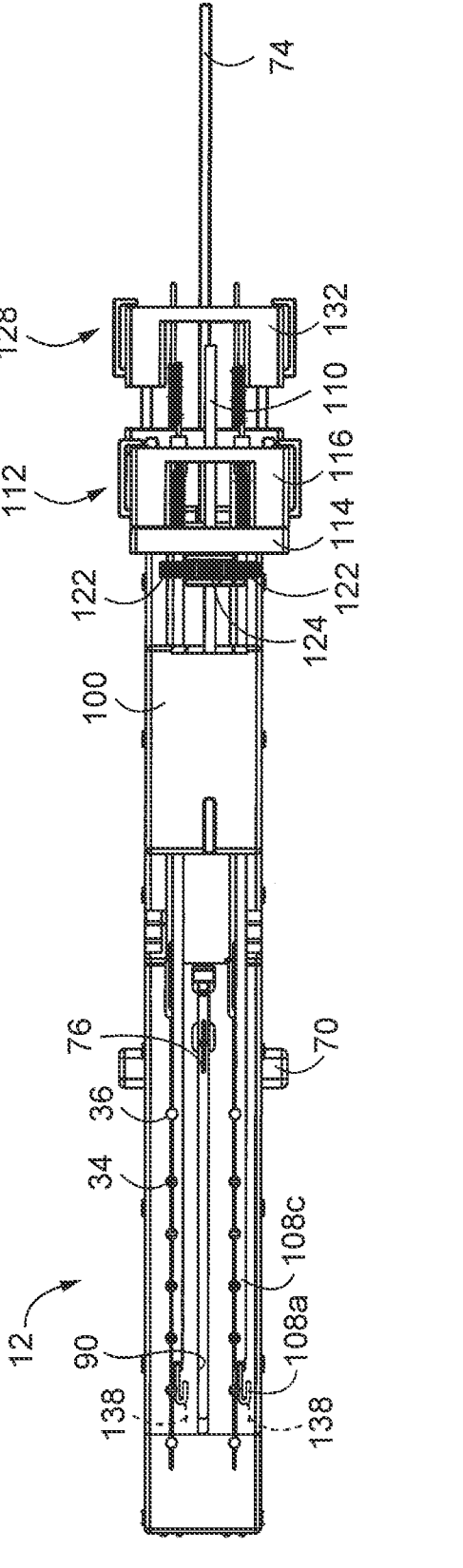
FIG. 19 is a view for explaining the operation of the suturing device of FIG. 1, wherein the upper-thread hooks are moved backward by a certain distance by a backward movement operation of an upper-thread hook operating portion.

Next, in response to the operation gear 124 being operated, the upper-thread hooks 108 are rotated clockwise by 90° with respect to the respective distal ends thereof to cause the hook portions 108*a* to be in a horizontal orientation in which the hook portions 108*a* are parallel to the third direction. In this state, in response to the wire connecting member 114 of the upper-thread hook operating portion 112 being operated to be further moved forward, as illustrated in FIG. 18, the hook portions 108*a* of the hook wires 108*b* protrude beyond the oblique end faces 108*d* of the hook pipes 108*c*, respectively, as illustrated in FIG. 18. In this state, the hook portions 108*a* have reached respective positions beyond the positions where the upper threads 138 are positioned by the upper-thread guide grooves 152*a*, respectively, illustrated in FIG. 2. Thus, the upper threads 138 enter inside the hook portions 108*a*, respectively. Next, in response to the upper-thread hook operating portion 112 being operated to be moved backward, the upper-thread hooks 108 are moved backward by a certain distance, and thus the upper threads 138 are positioned deep inside the hook portions 108*a*, respectively. FIG. 19 illustrates this state.

Figure 20:
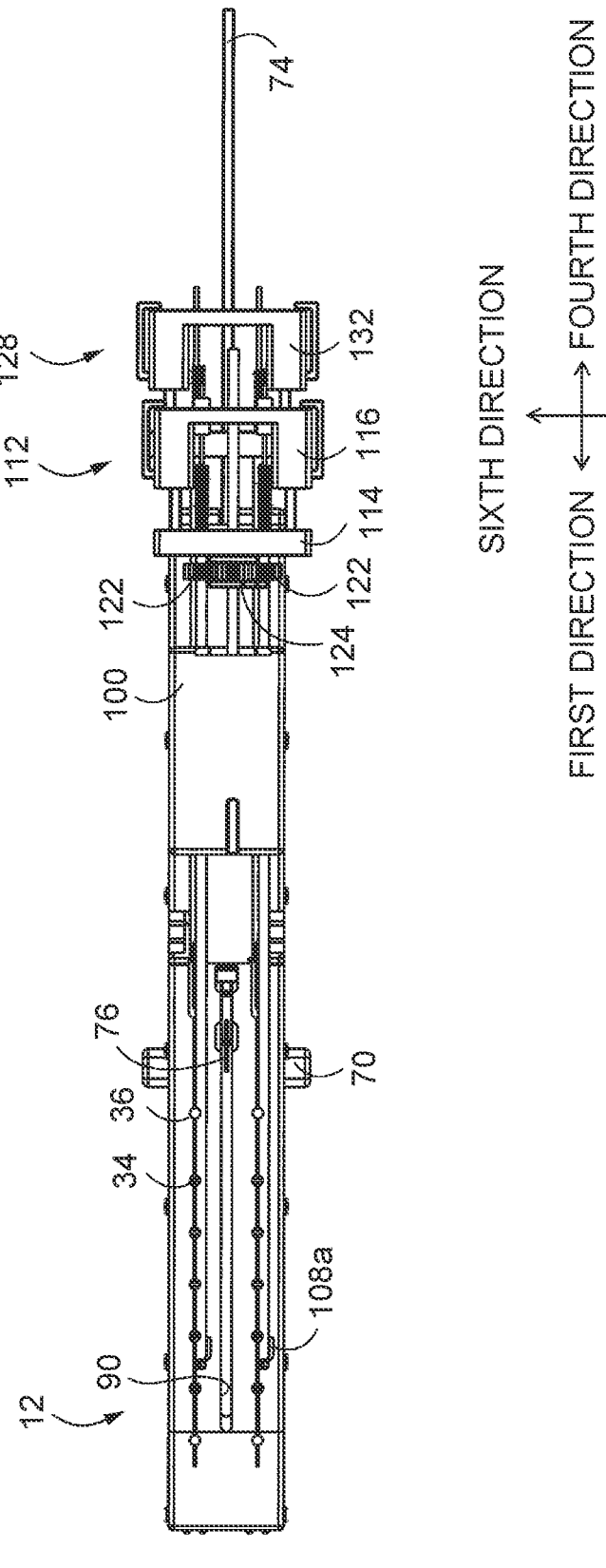
FIG. 20 is a view for explaining the operation of the suturing device of FIG. 1, wherein the hook portions of the hook wires are pulled into the oblique inclined faces of the hook pipes in response to a wire connecting member of the upper-thread hook operating portion being operated to move backward.
Figure 21:
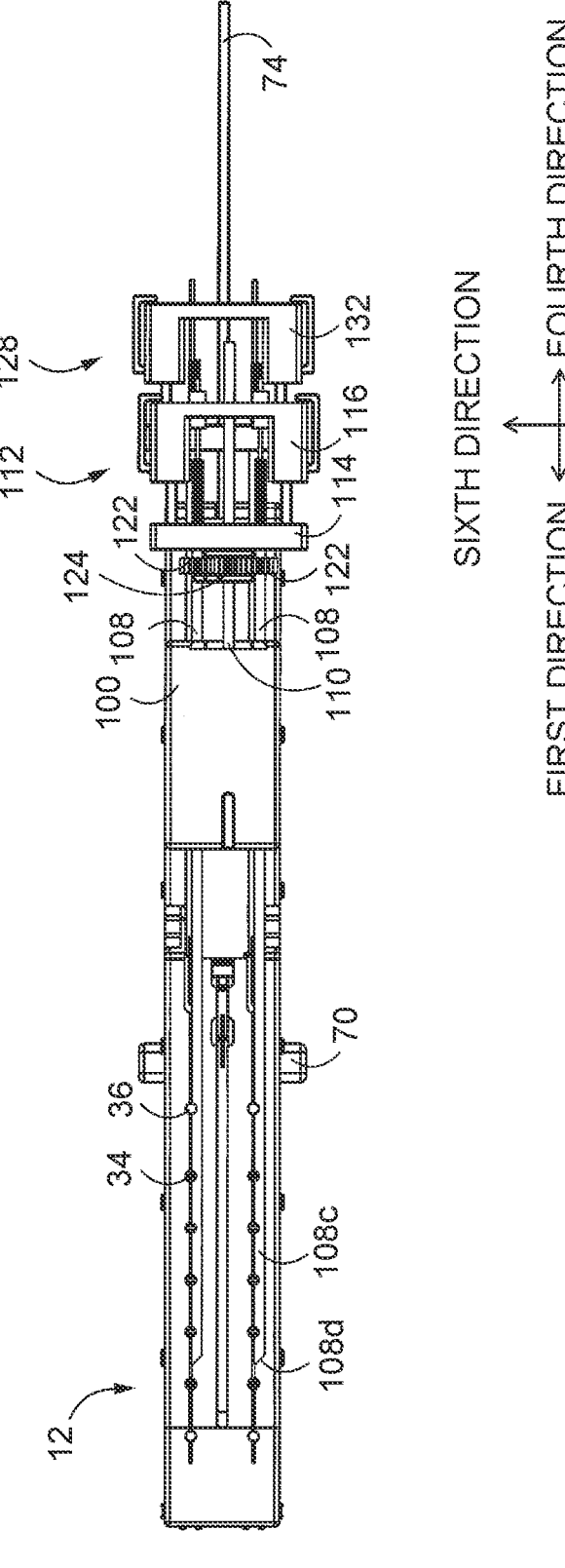
FIG. 21 is a view for explaining the operation of the suturing device of FIG. 1, wherein the upper-thread hooks are turned by 90° counterclockwise toward distal ends thereof by an operation of an operating gear.

Next, in response to the wire connecting member 114 of the upper-thread hook operating portion 112 being operated to be moved backward, as illustrated in FIG. 20, the hook portions 108*a* of the hook wires 108*b* are retracted so as not to protrude beyond the oblique end faces 108*d* of the hook pipes 108*c*. Thus, each of the upper threads 138 is held between the hook portion 108*a* and the oblique end face 108*d*. Next, in response to the operation gear 124 being operated, the upper-thread hooks 108 are rotated counterclockwise by 90° with respect to the respective distal ends thereof to cause the hook portions 108*a*, as illustrated in FIG. 21, to be in an orientation illustrated in FIG. 13.

Next, in response to the upper-thread hook operating portion 112 being operated to be moved backward, the upper-thread hooks 108 are moved backward in the fourth direction toward their original positions. Further, the needle operating member 70 is operated such that the suture needles 34 are retracted into the first casing 12 but the thread cutting needles 36 protrude from the first casing 12. Further, in response to the lower-thread hook operating portion 128 being operated to be moved backward in a state where the pipe connecting member 132 of the lower-thread hook operating portion 128 are in contact with the wire connecting member 130 by a forward movement of the pipe connecting member 132 of the lower-thread hook operating portion 128 and the lower-thread hooks 102 hold the lower threads 42, respectively, the lower-thread hooks 102 are moved backward, thereby tightening the lower threads 42. In addition, in response to the needle operating member 70 being operated to be moved backward, the suture needles 34 are retracted to be removed from the suture target T. FIG. 22 illustrates a second-thread suturing step and a needle removing step.

Next, in response to the cutter pusher 74 being operated, the cutter 76 is moved to a leading end, thereby cutting the suture target T. FIG. 23 illustrates this state. Next, in response to the needle operating member 70 being further operated to be moved backward such that the thread cutting needles 36 are retracted into the first casing 12, each set of the upper thread 138 and the lower thread 42 is cut by the cutting edge 56 of a corresponding thread cutting needle 36. FIG. 24 illustrates this state.

As described above, according to the suturing device 10 of the illustrative embodiment, the suturing device 10 includes the plurality of suture needles 34, a first-thread holding mechanism 84, a needle moving mechanism (e.g., the needle driving plates 60, 62, 64, 66), and a thread turning structure (e.g., the apexes 44*a*, 44*b*, and the third-direction guide groove 44*c*). The plurality of suture needles 34 are arranged in a row at certain intervals along the first direction and each have a distal end portion 44 formed with a thread hooking portion configured to allow the lower thread (e.g., the first thread) 42 to be hooked thereon. The first-thread holding mechanism holds the lower thread 42 to be engaged with the plurality of suture needles 34. The needle moving mechanism moves the suture needles 34 in the second direction intersecting the first direction. The second direction is a direction in which the distal end of each of the suture needles 34 is directed. In a state where the suture needles 34 have been moved in the second direction, in the lower thread 42 stretched in the first direction, the thread turning structure locally turns a portion of the lower thread 42 hooked on the distal end portion 44 of each of the suture needles 34 around the needle axis CN thereof such that the portion of the lower thread 42 extends in a direction along the third direction intersecting the first direction and the second direction. Each of the suture needles 34 has the side surface formed with the threading recessed groove 46 extending through the side surface in the first direction in a state where each of the suture needles 34 has been moved in the second direction. Prior to the suturing operation, in response to each of the suture needles 34 being moved in the second direction in a state where the lower thread (e.g., the first thread) 42 is linearly stretched and engaged with the distal end portions (e.g., the thread hooking portions) 44 of the suture needles 34, in the lower thread 42 stretched in the first direction, a portion of the lower thread 42 hooked on the distal end portion of each of the suture needles 34 is locally turned around the needle axis CN of each of the suture needles 34 to extend in the third direction by the thread turning structure (e.g., the apexes 44a, 44b, and the third-direction guide groove 44c). In this state, a thread loop R is formed at the opening of each of the threading recessed grooves 46 extending through the respective suture needles 34 in the first direction. Thus, suturing is performed at a stroke by pulling the lower thread (e.g., the first thread) 42 or the upper thread (e.g., the second thread) 138 to be threaded through the thread loops R. Since the operation of setting the lower thread 42 on the suture needles 34 is completed by engaging the lower thread 42 in the linearly stretched manner with the distal end portions of the suture needles 34 prior to such a suturing operation, the operation of setting the suture performed prior to the suturing operation is simplified.

According to the suturing device 10 of the illustrative embodiment, each of the threading recessed grooves 46 has the inclined surface 46a such that the groove bottom of the threading recessed groove 46 is shallower toward the distal end portion of each of the suture needles 34. Thus, when each of the suture needles 34 is removed from the suture target T, the threading recessed groove 46 is prevented from being caught on the suture target T, and thus each of the suture needles 34 is easily removed from the suture target T.

According to the suturing device 10 of the illustrative embodiment, the thread turning structure (e.g., the apexes 44a, 44b, and the third-direction guide groove 44c) includes the two apexes 44a, 44b, the third-direction guide groove 44c, and the two inclined guide surfaces 44d, 44e. The apexes 44a, 44b are formed at the distal end portion 44 of each of the suture needles 34 and allow the lower thread 42 to pass therebetween. The third-direction guide groove 44c extend in the third direction and is in communication with the space between the two apexes 44a, 44b. Each of the inclined guide surfaces 44d, 44e obliquely extend toward the third-direction guide groove 44c from the two apexes 44a, 44b. Thus, when each of the suture needles 34 is inserted into the suture target T, in the lower thread 42 hooked between the two apexes 44a and 44b formed at the distal end portion 44 of each of the plurality of suture needles 34, a portion of the lower thread 42 extending in the first direction that has passed the two apexes 44a and 44b is automatically guided to extend in the third direction by the third-direction guide groove 44c.

According to the suturing device 10 of the illustrative embodiment, in each of the suture needles 34, the third-direction guide groove 44c passes through the needle axis CN of the suture needle 34 and extends through the suture needles 34 in the third direction. The two apexes 44a and 44b are located on the respective sides of the third-direction guide groove 44c and are point symmetric with respect to the needle axis CN of the suture needle 34. The inclined guide surfaces 44d and 44e are point symmetric with respect to the needle axis CN of the suture needle 34. Thus, as the portion of the lower thread 42 extending in the first direction that is engaged between the two apexes 44a and 44b loosens into the third-direction guide groove 44c, the portion of the lower thread 42 is locally turned to extend in the third direction.

According to the suturing device 10 of the illustrative embodiment, the needle moving mechanism includes the needle stands 40a and a moving member (e.g., the needle driving plates 60, 62, 64, 66). The needle stands 40a are disposed in a casing (e.g., the first casing 12, the second casing 14) holding the plurality of suture needles 34. Each of the needle stands 40a is disposed at the proximal end portion 40 of a corresponding one of the suture needles 34 to support the corresponding suture needle 34. The moving member is movable along the first direction and the fourth direction opposite to the first direction of the casing. Each of the needle stands 40a includes the first engagement protrusions (e.g., first engagement portions) 40c and the second engagement protrusions (e.g., second engagement portions) 40d. The first engagement protrusions 40c are in engagement with the protrusion guide grooves 38, respectively, formed in the inner wall surfaces of the casing. The second engagement protrusions 40d are to be engaged with the needle driving cam grooves 68 formed in the moving member to drive each of the suture needles 34 in the protruding direction. In response to the moving member moving, the needle stands 40a are slid along the respective protrusion guide grooves 38 to move the corresponding suture needles 34 toward the distal end portions 44. Thus, in response to the moving member moving, the needle stands 40a are slid along the respective protrusion guide grooves 38, and thus, the suture needles 34 are moved toward the distal end portions 44. Therefore, in response to the movement of the needle driving plates 60, 62, 64, 66, the plurality of suture needles 34 are moved at a stroke in the second direction that is directed toward the distal-end side of the plurality of suture needles 34.

According to the suturing device 10 of the illustrative embodiment, the suturing device 10 includes the thread cutting needles 36, each of which is disposed such that the thread cutting needle 36 is arranged at the end position in the first direction in the row of the plurality of suture needles 34 arranged along the first direction. The thread cutting needle 36 has the side surface formed with the thread cutting recessed groove 54 extending through the side surface of the thread cutting needle 36 in the first direction. The thread cutting recessed groove 54 has the cutting edge 56 at the distal-end side position of the thread cutting needle 36. The cutting edge 56 faces the proximal end portion 50 side of the thread cutting needle 36. Thus, in response to each of the thread cutting needles 36 being pulled into the first casing 12, the lower thread 42 and the upper thread 138 that have been threaded into the thread loops are cut.

According to the suturing device 10 of the illustrative embodiment, the cutting edge 56 of the thread cutting recessed groove 54 obliquely extends toward the proximal end portion 50 of the thread cutting needle 36 as the cutting edge 56 extends toward the distal end of the cutting edge 56. Thus, when each of the thread cutting needles 36 is pulled into the first casing 12 toward the proximal end portion 50 side thereof, the lower thread 42 in the thread cutting recessed groove 54 is prevented from moving away therefrom, and thus the lower thread 42 is reliably cut.

According to the suturing device 10 of the illustrative embodiment, the suturing device 10 includes the first casing 12 and the second casing 14 that are openable and closable. The first casing 12 includes the suture needles 34, the lower threads 42, and the lower-thread bobbins (e.g., the first-thread holding mechanisms) 84. The first casing 12 includes the upper-thread hook (e.g., a first thread hook) 108 elongated in the first direction. The upper-thread hook is to be moved in the first direction and the fourth direction in the threading recessed grooves 46 formed in the side surfaces of the suture needles 34 in a state where the first casing 12 and the second casing 14 are closed. Thus, suturing is performed at a stroke by moving the upper-thread hook (e.g., the first thread hook) 108 that has caught the upper thread 138 or the lower thread 42 through the thread loops R formed to the third direction sides of the suture needles 34, respectively.

According to the suturing device 10 of the illustrative embodiment, the upper-thread hook (e.g., the first thread hook) 108 includes the tubular hook pipe (e.g., a tubular member) 108c and the hook wire (e.g., a hook member) 108b. The hook pipe 108c has the oblique end face 108d that is the distal end portion of the hook pipe 108c in the first direction cut obliquely in the plane including the first direction and the third direction such that the width of the hook pipe 108c in the third direction decreases toward the first direction. The oblique end face 108d opens in the first direction and the third direction. The hook wire 108b has the hook portion 108a that is the distal end of the hook wire 108b in the first direction bent into a U-shape. The hook wire 108b is disposed inside the hook pipe 108c so as to be relatively movable in the first direction and the fourth direction until the hook portion 108a contacts the oblique end face 108d of the hook pipe 108c. Thus, in a state where the upper thread 138 or the lower thread 42 is held between the hook portion 108a of the hook wire 108b and the oblique end face 108d of the hook pipe 108c, the upper thread 138 or the lower thread 42 is threaded through the thread loops R.

According to the suturing device 10 of the illustrative embodiment, the second casing 14 includes the upper-thread bobbins (e.g., second-thread holding mechanisms) 156, each of which holds the upper thread 138 at a position further to the first direction than the suture needle 34 located at an end in the first direction among the plurality of suture needles in a state where the first casing that holds the upper threads 138 (e.g., the second threads) at the distal end portion thereof in the first direction and the second casing are closed. The second casing 14 includes the suture needles 34, the lower threads 42, and the lower-thread bobbins (e.g., the first-thread holding mechanisms) 84. The first casing 12 includes the upper-thread hook (e.g., the first thread hook) 108 that is elongated in the first direction and is moved in the first direction and the fourth direction through the threading recessed grooves 46 formed in the side surfaces of the suture needles 34 in a state where the first casing 12 and the second casing 14 are closed. Therefore, in a state where the suture needles 34 have been moved in the second direction by the needle moving mechanisms such as the needle driving plates (e.g., the moving members) 60, 62, 64, and 66, the upper-thread hook (e.g., the first thread hook) 108 is moved through the threading recessed grooves 46 in the fourth direction after holding the upper thread 138. Thus, the suture target T is sutured by the lower thread 42 and the upper thread 138.

According to the suturing device 10 of the illustrative embodiment, the first casing includes the thread holes (e.g., first-thread guide grooves) 92, the lower-thread hooks (e.g., the second thread hooks) 102 and the thread retaining grooves (e.g., first-thread retaining grooves) 98. Each of the thread holes 92 guides the lower thread (e.g., the first thread) 42 supplied from the lower-thread bobbin (e.g., the first-thread holding mechanism) 84. Each of the lower-thread hooks 102 is movable in the first direction and the fourth direction and allows the lower thread 42 to be hooked thereon, the lower thread 42 extending from the thread retaining groove 98 via the distal end portion 44 of each of the suture needles 34. Each of the thread retaining grooves 98 retains an end portion of the lower thread 42 hooked on the lower-thread hook 102. Thus, each of the lower threads 42 is tightened by a corresponding one of the lower-thread hooks 102, thereby achieving suturing without looseness.

According to the suturing device 10 of the illustrative embodiment, the suturing device 10 includes an opening and closing mechanism (e.g., the bearings 16 and the pivot shafts 18) and a locking mechanism (e.g., the locking pipe engagement hole 106 and the locking pipe 110). The opening and closing mechanism maintains the closed state in which the suture target T is sandwiched between the first casing 12 and the second casing 14 or the open state in which the first casing 12 and the second casing 14 are separated from each other. The locking mechanism maintains the closed state of the first casing 12 and the second casing 14 maintained by the opening and closing mechanism. Thus, in puncturing of the suture target T with the plurality of suture needles 34, when the suture needles 34 in the first casing 12 are moved toward the second direction by the needle moving mechanism such as the needle driving plates (e.g., the moving members) 60, 62, 64, 66, the first casing 12 and the second casing 14 are restricted from opening.

According to the suturing device 10 of the illustrative embodiment, the locking mechanism (e.g., the bearings 16, and the pivot shafts 18) includes the pivot shafts 18 each having a pivot axis C. The pivot shafts 18 lock the second casing 14 to the first casing 12 at the end portion of the second casing 14, and allows the second casing 14 to pivot between the open state and the closed state. The locking mechanism (e.g., the locking pipe engagement hole 106 and the locking pipe 110) includes the locking pipe (e.g., the pivot prevention member) 110 and the locking pipe engagement hole 106 (e.g., an engagement hole) 106. The locking pipe 110 is an elongated member along the first direction. The locking pipe 110 is insertable into and removable from the second casing 14 in a direction intersecting the pivot axis C and prevents pivoting of the second casing 14 around the pivot axis C. The locking pipe engagement hole 106 is provided in the first casing 12 and allows the locking pipe 110 to be removably engaged therein. Thus, in puncturing of the suture target T with the plurality of suture needles 34, insertion of the pivot prevention member into the second casing 14 restricts the first casing 12 and the second casing 14 from opening.

According to a suturing method using the suturing device 10 of the illustrative embodiment, the method includes a first-thread hooking and setting step, a puncturing step, a first-thread suturing step, and a needle removing step. The first-thread hooking and setting step is linearly hooking the lower thread (e.g., the first thread) 42 on the distal end portion 44 of each of the plurality of suture needles 34 along the first direction prior to puncturing of the suture target T with the plurality of suture needles 34. The puncturing step is puncturing the suture target T with the plurality of suture needles 34 and locally turning the portion of the lower thread 42 hooked on each of the suture needles 34 such that the portion of the lower thread 42 extends in the third direction orthogonal to the first direction, thereby positioning the first thread at the opening of each of the threading recessed grooves 46. The first-thread suturing step is moving the thread hook 108 in the fourth direction opposite to the first direction in a state where the lower thread (e.g., the first thread) 42 is hooked on the distal end portion of the thread hook 108 that has been moved in the first direction to pass through each of the threading recessed grooves 46, thereby threading the lower thread 42 through the thread loops R formed by the lower thread 42 at the suture needles 34, respectively. The needle removing step is removing the suture needles 34 from the suture target T. Prior to the suturing operation, in response to each of the suture needles 34 being moved in the second direction in a state where the lower thread 42 is linearly stretched and hooked on the distal end portions (e.g., the thread hooking portions) 44 of the suture needles 34, in the lower thread 42 stretched in the first direction, a portion of the lower thread 42 hooked on the distal end portion (e.g., the thread hooking portion) 44 of each of the suture needles 34 is locally turned around the needle axis CN of each of the suture needles 34 to extend in the third direction by the thread turning structure (e.g., the apexes 44a, 44b, and the third-direction guide groove 44c). In this state, thread loops R are formed at the openings of the threading recessed grooves 46 extending through the suture needles 34 in the first direction. Thus, suturing is performed at a stroke by moving the thread hook 108 through the threading recessed grooves 46 to thread the lower thread 42 and the upper thread 138 into the thread loops R. Prior to such a suturing operation, the operation of setting the lower thread 42 on the suture needles 34 is completed by hooking the lower thread 42 in the linearly stretched manner on the distal end portion (e.g., the thread hooking portion) 44 of each of the suture needles 34. Thus, the operation of setting the suture thread performed prior to the suturing operation is simplified.

According to a suturing method using the suturing device 10 of the illustrative embodiment, the method includes a first-thread hooking and setting step, a puncturing step, a second-thread suturing step, and a needle removing step. The first-thread hooking and setting step is linearly hooking the lower thread (e.g., the first thread) 42 on the distal end portion 44 of each of the plurality of suture needles 34 along the first direction prior to puncturing of the suture target T with the plurality of suture needles 34. The puncturing step is puncturing the suture target T with the plurality of suture needles 34 and locally turning the portion of the lower thread 42 hooked on each of the suture needles 34 to extend in the third direction orthogonal to the first direction to position at the opening of each of the threading recessed grooves 46. The second-thread suturing step is moving the thread hook 108 through each of the threading recessed grooves 46 in the fourth direction opposite to the first direction in a state where the upper thread (e.g., the second thread) 138 is hooked on the distal end portion of the thread hook 108 that has been moved in the first direction, thereby threading the upper thread 138 through the thread loops R formed by the lower thread 42 at the suture needles 34, respectively. The needle removing step is removing the suture needles 34 from the suture target T. Prior to the suturing operation, in response to each of the suture needles 34 being moved in the second direction in a state where the lower thread 42 is linearly stretched and hooked on the distal end portions (e.g., the thread hooking portions) 44 of the suture needles 34, in the lower thread 42 stretched in the first direction, a portion of the lower thread 42 hooked on the distal end portion (e.g., the thread hooking portion) 44 of each of the suture needles 34 is locally turned around the needle axis CN of each of the suture needles 34 to extend in the third direction by the thread turning structure (e.g., the apexes 44a, 44b, and the third-direction guide groove 44c). In this state, thread loops R are formed at the openings of the threading recessed grooves 46 extending through the suture needles 34 in the first direction. Thus, suturing is performed at a stroke by moving the thread hook 108 through the threading recessed grooves 46 to thread the lower thread 42 and the upper thread 138 into the thread loops R. Prior to such a suturing operation, the operation of setting the lower thread 42 on the suture needles 34 is completed by hooking the lower thread 42 in the linearly stretched manner on the distal end portion (e.g., the thread hooking portion) 44 of each of the suture needles 34. Thus, the operation of setting the suture thread performed prior to the suturing operation is simplified.

ILLUSTRATIVE EMBODIMENT 2

FIG. 25 is a perspective view illustrating another suture needle 234 used in place of the suture needles 34. The suture needle 234 of the illustrative embodiment has commonalities with the suture needles 34. The suture needle 234 has two apexes 244a and 244b spaced apart in the third direction, a third-direction guide groove 244c between the two apexes 244a and 244b, and a threading recessed groove 246 extending therethrough in the first direction. However, the suture needle 234 has a different structure from the suture needle 34 in that heights of the two apexes 244a and 244b are different from those in the suture needle 34 and a groove bottom of the third-direction guide groove 244c does not have a convex surface but a flat surface.

Although the illustrative embodiments of the disclosure have been described above with reference to the drawings, the disclosure is also applied to other embodiments.

For example, a natural thread, a synthetic thread, a metallic thread, or a composite thread is used as the above-described upper threads 138 and lower threads 42. The natural thread is a monofilament or multifilament thread made from plant or animal fibers. The synthetic thread is a monofilament or multifilament thread made of synthetic fibers. The metallic thread is a monofilament or multifilament thread made of metallic wires. The composite thread is made of natural fibers and synthetic fibers.

In the above-described illustrative embodiments, the third-direction guide groove 44c formed in the distal end portion 44 of each of the suture needles 34 and opened between the pair of apexes 44a and 44b is used as the thread turning structure for locally turning a portion of the lower thread 42 extending in the first direction hooked between the pair of apexes 44a and 44b provided at the distal end of each of the suture needles 34 such that the portion of the lower thread 42 extends in the third direction. However, another thread turning structure may be adopted in which each of the suture needles 34 is rotated by 90° about the needle axis CN to locally turn a portion of the lower thread 42 extending in the first direction hooked between the pair of apexes 44a and 44b provided at the distal end of each of the suture needles 34 such that the portion of the lower thread 42 extends in the third direction. That is, according to the suturing device 10 of the illustrative embodiment, the distal end portion 44 of each of the suture needles 34 may have the two apexes 44a and 44b that allow the lower thread 42 to pass therebetween and a first-direction retaining recessed groove 44c between the two apexes 44a and 44b. The thread turning structure may include a suture needle rotating mechanism that rotates each of the suture needles 34 about the needle axis CN of a corresponding one of the suture needles 34 to turn the first-direction retaining recessed groove 44c formed between the two apexes 44a and 44b at the distal end portion 44 of the suture needle 34 such that the portion of the lower thread 42 extends in the third direction. In this case, also, a portion of the lower thread 42 in the first direction hooked on the first-direction retaining recessed groove 44c formed between the two apexes 44a and 44b is locally turned to extend in the third direction as the suture needle 34 is turned by the suture needle rotating mechanism.

Further, in the above-described illustrative embodiments, the lower thread 42 and the upper thread 138 are used for suturing, but suturing using only the lower thread 42 may be performed by performing the first-thread suturing step instead of the above-described second-thread suturing step. For example, in a state where the suture needles 34 have been moved in the second direction by the needle moving mechanism such as the needle driving plates (e.g., the moving members) 60, 62, 64, 66, the hook wire 108b is retracted into the hook pipe 108c with the hook portion 108a of the hook wire 108b hooking the lower thread 42 constituting the thread loop R formed by the suture needle 34 located at an end in the first direction among the plurality of suture needles. Thus, the lower thread 42 is held between the hook portion 108a of the hook wire 108b and the oblique end face 108d of the hook pipe 108c. Thereafter, the upper-thread hook (e.g., the first thread hook) 108 is moved through the threading recessed grooves 46 in the fourth direction. Thus, suturing using the lower thread 42 only is performed at a stroke by the first-thread suturing step.

In the above-described illustrative embodiments, the first casing 12 and the second casing 14 both have a rectangular shape in cross section. Nevertheless, the first casing 12 and the second casing 14 may be tubular members each having a circular shape, an oval shape, or a polygonal shape in cross section.

In the above-described illustrative embodiments, the shapes of the operating members 70, 110a, 112, and 128 may be changed to, for example, respective shapes suitable for remote operation. The shape of the operating members 70, 110a, 112, and 128 may be changed respective shapes capable of connecting thereto an actuator for electrically driving and controlling a corresponding operating member.

Although the suture needles 34 are arranged in two rows in the suturing device 10, but may be arranged in a single row or three or more rows.

While the disclosure has been described in detail with reference to the specific embodiments thereof, these are merely examples, and various changes, arrangements and modifications may be applied therein without departing from the spirit and scope of the disclosure.

What is claimed is:

1. A suturing device, comprising:
a plurality of suture needles arranged in a row at certain intervals along a first direction, the plurality of suture needles each having a distal end portion formed with a thread hooking portion configured to allow a first thread to be hooked thereon;
a first-thread holding mechanism configured to hold the first thread to be engaged with the plurality of suture needles;
a needle moving mechanism configured to move the plurality of suture needles in a second direction intersecting the first direction, the second direction being a direction in which a distal end of each of the plurality of suture needles is directed; and
a thread turning structure configured to locally turn a portion of the first thread hooked on the distal end portion of each of the plurality of suture needles in the first thread stretched in the first direction around a needle axis thereof such that the portion of the first thread extends in a direction along a third direction intersecting the first direction and the second direction, in a state where the plurality of suture needles have been moved in the second direction,
wherein each of the plurality of suture needles has a side surface formed with a threading recessed groove extending through the side surface in the first direction in the state where each of the plurality of suture needles has been moved in the second direction.

2. The suturing device according to claim 1, wherein the threading recessed groove has an inclined surface such that a groove bottom of the threading recessed groove is shallower toward the distal end of each of the plurality of suture needles.

3. The suturing device according to claim 1, wherein the thread turning structure includes:
two apexes formed at the distal end portion of each of the plurality of suture needles, the two apexes configured to allow the first thread to pass therebetween;
a third-direction guide groove extending in the third direction and being in communication with a space between the two apexes; and
two inclined guide surfaces obliquely extending toward the third-direction guide groove from the two apexes.

4. The suturing device according to claim 3, wherein the two apexes are point symmetric with respect to an axis of each of the plurality of suture needles and the two inclined guide surfaces are point symmetric with respect to the axis of each of the plurality of suture needles.

5. The suturing device according to claim 1, wherein
the distal end portion of each of the plurality of suture needles has:
two apexes configured to allow the first thread to pass therebetween; and
a first-direction retaining recessed groove between the two apexes, and
the thread turning structure includes a suture needle rotating mechanism configured to rotate each of the plurality of suture needles about an axis of a corresponding one of the plurality of suture needles to turn the first-direction retaining recessed groove formed between the two apexes such that the first-direction retaining recessed groove extends in the third direction.

6. The suturing device according to claim 1, wherein
the needle moving mechanism includes:
a plurality of needle stands disposed in a casing holding the plurality of suture needles, each of the plurality of needle stands being disposed at a proximal end side of a corresponding one of the plurality of suture needles to support the corresponding one of the plurality of suture needles; and
a moving member movable along the first direction and a fourth direction of the casing, the fourth direction being opposite to the first direction,
each of the plurality of needle stands includes:
a first engagement portion being in engagement with a guide portion formed in an inner wall surface of the casing; and
a second engagement portion to be engaged with a needle driving cam groove formed in the moving member, the needle driving cam groove configured to drive each of the plurality of suture needles in the second direction, and
in response to the moving member moving, each of the plurality of needle stands is slid along the guide portion to move a corresponding one of the plurality of suture needles in the second direction.

7. The suturing device according to claim 1, further comprising a thread cutting needle disposed such that the thread cutting needle is arranged at an end position in the first direction in the row of the plurality of suture needles arranged in the row along the first direction, wherein the thread cutting needle has a side surface formed with a thread cutting recessed groove extending through the side surface of the thread cutting needle in the first direction, the thread cutting recessed groove having a cutting edge at a distal-end-side position of the thread cutting needle, the cutting edge facing a proximal-end side of the thread cutting needle.

8. The suturing device according to claim 7, wherein the cutting edge of the thread cutting recessed groove obliquely extends toward the proximal-end side of the thread cutting needle as the cutting edge extends toward a distal end of the cutting edge.

9. The suturing device according to claim 1, further comprising a first casing and a second casing both being openable and closable, wherein the first casing includes the plurality of suture needles, the first thread, and the first-thread holding mechanism, and the second casing includes a first thread hook being elongated in the first direction and movable in the first direction and a fourth direction in the threading recessed groove formed in the side surface of each of the plurality of suture needles in a state where the first casing and the second casing are closed, the fourth direction being opposite to the first direction.

10. The suturing device according to claim 9, wherein the first thread hook includes:

a tubular member having an oblique end face that is a distal end portion of the tubular member in the first direction cut obliquely in a plane including the first direction and the third direction such that a width of the tubular member in the third direction decreases toward the first direction, the oblique end face opening in the first direction and the third direction;

a hook member having a hook portion that is a distal end portion of the hook member in the first direction bent into a U-shape, the hook member being disposed inside the tubular member so as to be relatively movable in the first direction and the fourth direction until the hook portion contacts the oblique end face of the tubular member.

11. The suturing device according to claim 10, wherein in a state where each of the suture needles has been moved in the second direction by the needle moving mechanism, while the hook portion hooks thereon the first thread constituting a thread loop formed by a suture needle of the plurality of suture needles, the suture needle being located at an end in the first direction among the plurality of suture needles, the hook member is relatively moved in the tubular member until the hook member contacts the oblique end face of the tubular member, to hold the first thread between the hook portion and the oblique end face, and then the first thread hook is rotated to a position where the oblique end face faces toward a fifth direction opposite to the second direction and is moved through the threading recessed groove of each of the suture needles in the fourth direction.

12. The suturing device according to claim 10, wherein the second casing includes a second-thread holding mechanism holding a second thread at a position further to the first direction than a suture needle of the plurality of suture needles, the suture needle being located at an end in the first direction among the plurality of suture needles, in a state where the first casing and the second casing are closed, and in a state where each of the suture needles has been moved in the second direction by the needle moving mechanism, while the hook portion hooks thereon the second thread after holding the second thread, the hook member is retracted into the tubular member to hold the second thread between the hook portion and the oblique end face, and then the first thread hook is rotated to a position where the oblique end face faces toward a fifth direction opposite to the second direction and is moved through the threading recessed groove of each of the suture needles in the fourth direction.

13. The suturing device according to claim 12, wherein the first casing includes:

a first-thread guide groove configured to guide the first thread supplied from the first-thread holding mechanism;

a second thread hook being movable in the first direction and the fourth direction and configured to allow the first thread to be hooked thereon, the first thread extending from the first-thread guide groove via the distal end portion of each of the plurality of suture needles; and a first-thread retaining groove configured to retain an end portion of the first thread hooked on the second thread hook.

14. The suturing device according to claim 9, further comprising:

an opening and closing mechanism configured to maintain a closed state in which a suture target is sandwiched between the first casing and the second casing or an open state in which the first casing and the second casing are separated from each other; and a locking mechanism configured to maintain the closed state of the first casing and the second casing maintained by the opening and closing mechanism.

15. The suturing device according to claim 14, wherein the opening and closing mechanism includes a pivot axis configured to lock the second casing to the first casing at an end portion of the second casing and to allow the second casing to pivot between the open state and the closed state, and the locking mechanism includes:

a pivot prevention member being an elongated member along the first direction, the pivot prevention member being insertable into and removable from the second casing in a direction intersecting the pivot axis, the pivot prevention member configured to prevent pivoting of the second casing around the pivot axis; and an engagement hole being provided in the first casing and configured to allow the pivot prevention member to be removably engaged therein.

\* \* \* \* \*